(12) United States Patent
Grant et al.

(10) Patent No.: US 6,514,709 B1
(45) Date of Patent: *Feb. 4, 2003

(54) HIGH THROUGHPUT SCREENING BY MEASUREMENT OF INTRACELLULAR CALCIUM LEVELS

(75) Inventors: Stephan K. Grant, East Windsor, NJ (US); Gregory J. Kaczorowski, Edison, NJ (US); Richard E. Middleton, Gillette, NJ (US)

(73) Assignee: Merck & Co., Inc., Rahway, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/805,285

(22) Filed: Mar. 13, 2001

Related U.S. Application Data

(60) Provisional application No. 60/188,869, filed on Mar. 13, 2000.

(51) Int. Cl.$^7$ .......................... G01N 33/53; C12Q 1/68
(52) U.S. Cl. .................................. 435/7.1; 435/6; 435/4
(58) Field of Search ................. 435/7.1, 6, 4; 536/23.1; 530/350

(56) References Cited

U.S. PATENT DOCUMENTS

5,858,713 A  1/1999  Soderlund et al.
5,942,407 A  8/1999  Liotta et al.

OTHER PUBLICATIONS

Lin et al. Rapid Measurements of intracellular calcium using a fluorescence plate reader. Biotechniques 26:318–326, 1999.*
Button and Brownstein Aequorin–expressing mammalian cell lines used to report Ca2+ mobilization. Cell Calcium, 14: 663–671, 1993.*
Collatz et al. Intracellular calcium chelator BAPTA protects cells against toxic calcium overload but also alters physiological calcium responses. Cell Calcium 21:453–459, 1997.*
Keller, J. N. et al., "Increased Sensitivity to Mitochondrial Toxin–Induced Apoptosis . . . and Enhanced Oxyradical Production" J. Neurosci 18(12) p. 4439–4450, 1998.
Bednarek, M. A. et al., "Structure–Function Studies on the New Growth Hormone . . . Secretagogue Receptor 1a" J. Med. Chem., 43, p. 4370–4376, 2000.
Smith, R. G. et al., "Adenosine: A Partial Agonist of the Growth Hormone Secretagogue Receptor" Biochem Biophys. Res. Commun. 276, p. 1306–1313, 2000.
Tymianski, M. et al., "Cell–Permeant Ca Chelators Reduce Early Excitotoxic and ischemic Neuronal Injury In Vitro and In Vivo", Neuron, 11, p. 221–235, Aug. 1993.
Collatz, M.B. et al., "Intracellular Calcium Chelator BAPTA . . . calcium responses" Cell Calcium, 21, p. 453–459, 1997.
Caulfield, M.P. "Muscarinic Receptors–Characterization, Coupling and Function", Pharmac Ther. 58, p. 319–379 1993.
Prasher, D. et al., "Cloning and Expression of the cDNA Coding for Aequorin, A Bioluminescent Calcium–Binding Protein" Biochemical and Biophysical Research Communications, vol. 126, No. 3, pp. 1259–1268, 1985.
Lambert, D. G. "Calcium Signaling Protocols" Methods in Mol Biol 114, p. 125–133, 1999.
Tymianski, M. et al. "Properties of Neuroprotective Cell . . . Neurotoxicity In Vitro" J Neurophysiol 72(4) p. 1973–1992. 1994.
Tsien, R. Y. "A Non–Disruptive Technique for Loading Calcium Buffers and Indicators into Cells" Nature 290, p. 527–528, 1981.
Button, D. et al. "Aequorin–Expressing Mammalian Cell Lines Used To Report Ca Mobilization" Cell Calcium 14, p. 663–671, 1993.
Caterina, M. J. et al, "The Capsaicin Receptor: A Heat–Activated Ion Channel in the Pain Pathway" Nature 389, p. 816–824, 1997.
Takahashi, A. et al. "Measurement of Intracellular Calcium" Physiological Reviews 79, p. 1089–1125, 1999.
Ungrin, M.D. et al. "An Automated Aequorin Luminescence–Based Functional Calcium Assay for G–Protein–Coupled Receptors", Analytical Biochem 272 p. 34–42 1999.
Stables, J. et al. "A Bioluminescent Assay for Agonist Activity at Potentially Any G–Protein–Coupled Receptor" Analytic Biochem 252 p. 115–126, 1997.
Tsien, R. Y. "New Calcium Indicators and Buffers . . . Prototype Structures" Biochemistry 19 p. 2396–2404, 1980.
Struk, A. et al. "Fura–2 Calcium Signals . . . Concentrations of EGTA", Cell Calcium 23(1) p. 23–32, 1998.
Gonzalez, J. E. et al. "Cell–based Assays and Instrumentation for Screening Ion–Channel Targets" Drug Discovery Today vol. 4, No. 9, p. 431–439, 1997.
Creton, R. et al. "Calcium Imaging with Chemiluminescence" Micro. Res. Tech. 46, p. 390–397, 1985.
Miyawaki, A. et al. "Fluorescent Indicators for Ca Based on Green Fluorescent Proteins and Calmodulin" Nature vol. 388, p. 882–887, 1999.

* cited by examiner

Primary Examiner—Elizabeth Kemmerer
Assistant Examiner—Ruixiang Li
(74) Attorney, Agent, or Firm—Michael D. Yablonsky; Jack L. Tribble

(57) ABSTRACT

The present invention provides assays in which intracellular chelators are used to alter the kinetics of signal generation triggered by divalent cations, particularly calcium influx into the cell. The use of an intracellular chelator in the assay can delay and prolong the signal, allowing the signal to be detected by automated instrumentation without the need for simultaneous liquid handling at the time of detection.

10 Claims, 10 Drawing Sheets

HIGH THROUGHPUT SCREENING BY MEASUREMENT OF INTRACELLULAR CALCIUM LEVELS

CROSS-REFERENCE TO RELATED APPLICATIONS

This application claims the benefit of U.S. Provisional Application No. 60/188,869, filed Mar. 13, 2000, the contents of which are incorporated herein by reference in their entirety.

STATEMENT REGARDING FEDERALLY-SPONSORED R&D

Not applicable.

REFERENCE TO MICROFICHE APPENDIX

Not applicable.

FIELD OF THE INVENTION

The invention relates to assays in which intracellular chelators are used to alter the kinetics of signal generation triggered by divalent cations, particularly calcium.

BACKGROUND OF THE INVENTION

A variety of cell-based functional assays utilize measurements of intracellular calcium concentration to evaluate the activity of proteins in a normal physiological environment. These include assay for G-protein coupled receptors (GPCR) and plasma membrane ion channels. The large and rapid increase in intracellular calcium concentration by stimulation of these receptors and ion channels can be detected by intracellular calcium-sensitive probes, including fluorescent dyes, calcium-binding proteins such as the bioluminescent protein, aequorin, and modified green fluorescent protein-calmodulin chimer (Ungrin, M. D., Singh, L. M. R., Stocco, R., Sas, D. E., Abramovitz, M. (1999) An automated aequorin luminescence-based functional calcium assay for G-protein-coupled receptors. *Anal. Biochem.* 272, 34–42; Takahashi, A., Camacho, P., Lechleiter, J. D., and Herman, B. (1999) Measurement of intracellular calcium. *Physiological Reviews* 79, 1089–1125; Gonzalez, J. E., Oades, K., Leychis, Y. Harootunian, A., and Negulescu, P. (1999) Cell-based assays and instrumentation for screening ion-channel targets. *Drug Discovery Today* 4, 431–439; Miyawaki, A., Liopsi, J., Heim, R., McCaffery, J. M., Adams, J. A., Ikura, M., and Tsien, R. Y. (1997) Fluorescent indicators for $Ca^{2+}$ based on green fluorescent proteins and calmodulin. *Nature* 388, 882–887; Creton, R., Kreiling, J. A., and Jaffe, L. F. (1999) Calcium imaging with chemiluminescence. *Microsc. Res. Tech.* 46, 390–397; Prasher, D., McCann, R. O., and Cormier, M. J. (1985) Cloning and expression of the cDNA coding for aequorin, A bioluminescent calcium-binding protein. *Biochem. Biophys. Res. Commun.* 126, 1259–1268).

The detection of rapid and transient changes in intracellular calcium concentration requires instrumentation that simultaneously mixes a stimulant with cells and immediately detects the change in fluorescence or luminescence from the calcium reporter. This requirement for simultaneous liquid dispensing and signal detection has limited the application of these calcium transient measurements in cell-based functional assays due to lack of affordable instrumentation. The present invention demonstrates the utility of an intracellular calcium chelating agent to delay and/or prolong the calcium signaling response in a high density screening format such as 96-well, 384-well, 1526-well or 3456-well microtiter plates. The altering of the kinetics of the calcium signal in the presence of the chelator maintains the integrity of the assay while providing greater time for measuring the transient signal after addition of the stimulant. Therefore high throughput screening functional assays can also be performed on a greater variety of laboratory instruments.

Practitioners in the art of screening have been attempting to provide for methods to extend the time available to measure fluorescent or luminescent signals. For example, one idea was to add a reagent to alter or slow the kinetics of a cellular reporter enzyme reaction. Examples of this approach are the transformation of flash luciferase-based luminescence to glow-luminescence formats such as the PACKARD LUCLITE® Luciferase Reporter Gene Assay Kit (see U.S. Pat. No. 5,618,682 and EPO Patent Application 94 102 080.2) or PROMEGA STEADY-GLO™ Luciferase Assay System (see U.S. Pat. No. 5,283,179).

Intracellular chelators of calcium are used routinely to eliminate calcium responses in a number of systems but the kinetics of intracellular calcium responses have primarily been described in the absence of chelators (Takahashi, A., Camacho, P., Lechleiter, J. D., and Herman, B. (1999) Measurement of intracellular calcium. *Physiological Reviews* 79, 1089–1125; Struk, A., Szucs, G., Kremmer, H., and Melzer, W. (1998) Fura-2 calcium signals in skeletal muscle fibres loaded with high concentrations of EGTA. *Cell Calcium* 23, 23–32; Keller, J. N., Guo, Q., Holtsberg, F. W., Bruce-Keller, A. J., and Mattson, M. P. (1998) Increased sensitivity to mitochondrial toxin-induced apoptosis in neural cells expressing mutant presenilin-1 is linked to perturbed calcium homeostasis and enhanced oxyradical production. *J. Neurosci.* 18, 4439–4450). However, in attempts to understand the neuro-protective properties of BAPTA-AM, this chelator's effects on intracellular calcium transients has been studied in some detail (Tymianski, M., Wallace, M. C., Spigelman, I., Uno, M., Carlen, PI L., Tator, Ch H., and Charlton, M. P. (1993) Cell-permeant $Ca^{2+}$ chelators reduce early excitotoxic and ischemic neuronal injury in vitro and in vivo. *Neuron* 11, 221–235). For example, when high concentrations of glutamate were used to stimulate mouse spinal cord neurons, BAPTA-AM was protective, and primarily affected the fast transient by decreasing the amplitude and delaying the rise and decay time of the transient (Tymianski, M., Charlton, M. P., Carlen, P. L., and Tator, C. H. (1994) Properties of neuroprotective cell-permeant $Ca^{2+}$ chelators: Effects on $[Ca^{2+}]_i$ and glutamate neurotoxicity in vitro. *J. Neurophys.* 72, 1973–1992). Similar results were obtained using ionomycin-induced calcium influx where observed calcium transients were up to 8-fold slower in the presence of BAPTA-AM (Collatz, M. B., Rudel, R., and Brinkmeier H. (1997) Intracellular calcium chelator BAPTA protects cells against toxic calcium overload but also alters physiological calcium responses. *Cell Calcium* 21, 453–459).

It has now been discovered that buffering intracellular calcium with a calcium binding reagent can delay and/or prolong the calcium signaling response in a manner that can be practically applied to high throughput screening assays.

SUMMARY OF THE INVENTION

The present invention provides assays in which intracellular chelators are used to alter the kinetics of signal generation triggered by divalent cations, particularly calcium accumulation in the cell cytoplasm. The use of an intracellular chelator in the assay can delay and prolong the signal, allowing the signal to be detected by automated instrumentation without the need for simultaneous liquid handling at the time of detection.

An aspect of this invention is a high throughput assay in which cells having a receptor, which upon activation induces a calcium influx into the cell, are contacted with an intracellular calcium chelator. In preferred embodiments the chelator is 1,2-bis(o-aminophenoxy)ethane-N,N,N',N'-tetraacetic acid tetra(acetoxymethyl)ester (BAPTA-AM). In particular embodiments, the cells also contain an aequorin-based or fluorescent dye-based or green fluorescent protein-calmodulin chimer- based signal generation system. In a preferred embodiment, the assay is conducted in a microtiter plate format and an instrument is used to detect the signal in each well.

By "about" it is meant within 10% to 20% greater or lesser than particularly stated.

As used herein an "agonist" is a compound or molecule that interacts with and stimulates an activity of a receptor.

As used herein an "antagonist" is a compound that interacts with a receptor and inhibits or interferes with the activation of the receptor.

As used herein an "inhibitor" is a compound that interacts with and inhibits or prevents the activation of a receptor.

All of the references cited herein are incorporated by reference in their entirety as background material.

DETAILED DESCRIPTION OF THE INVENTION

Figure 1:
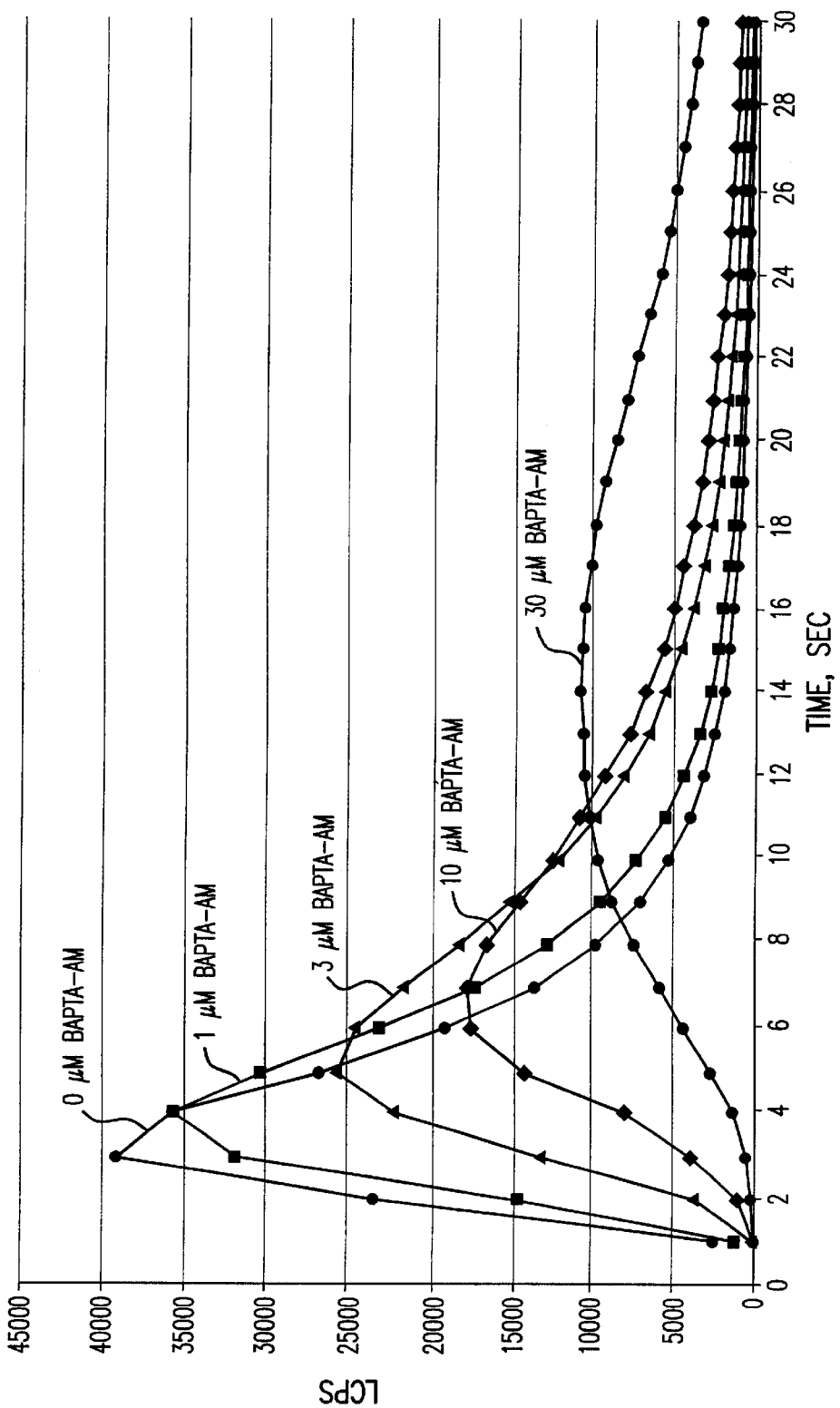
FIG. 1 shows kinetics of the calcium dependent luminescence upon the addition of an intracellular chelator in an assay using an ion channel coexpressed with apoaequorin.

The present invention provides assays in which intracellular chelators are used to alter the kinetics of signal generation triggered by divalent cations, particularly calcium influx into the cell. The use of an intracellular chelator in the assay can delay and prolong the signal, allowing the signal to be detected by automated instrumentation without the need for simultaneous liquid handling at the time of detection.

The present invention is generally applicable for measuring intracellular levels of calcium whether by fluorescence, luminescent or other detection techniques because the particular receptor, enzyme or reaction is not inhibited directly, only the kinetics of signal generation is changed by altering the levels of free calcium. While specific calcium chelators such as BAPTA and EGTA have been extensively used to buffer both extracellular and intracellular calcium levels the present invention employs intracellular chelators to affect the kinetics of the calcium-sensitive reporter (whether protein, enzyme or chemical). The result is that the signal is delayed and extended. In addition the invention has particular application to high throughput screening and whole cell functional assays for compounds with biological activity.

In the most general premise, one can use any type of protein or compound that can rapidly bind and sequester intracellular calcium. One can test whether a particular calcium binding reagent is appropriate by testing it in an assay taught herein and comparing the result to the assay performed using BAPTA-AM.

The invention includes the use of cell permeable calcium chelators00, such as BAPTA-AM, 1,2-bis(o-aminophenoxy)ethane-N,N,N',N'-tetraacetic acid tetra(acetoxymethyl)ester, to regulate changes in cellular calcium levels. The process is applicable to screening for compounds with biological activity where rapid and transient changes in cellular calcium are measured. Examples include the evaluation of receptor agonists or antagonists for calcium ion channels or G-protein coupled receptors (GPCR's) which elicit changes in cellular calcium concentration. The addition of the calcium chelator BAPTA-AM to the cells buffers the calcium response and alters the kinetics of the calcium signal as measured by intracellular reporters such as the calcium-sensitive bioluminescent aequorin protein or fluorescent proteins or synthetic probes such as the fluorescent calcium dyes (Fura 2, Fluo 3, Quin 2, Indo 1, etc.).

When an intracellular calcium chelator such as BAPTA-AM is added to cells (1–50 uM) the stimulation of the receptors is unaffected but the signal generated by the reporters is delayed due to the buffering of free calcium concentration by chelation. The outcome is the delay of the calcium-dependent signal (such as luminescence or fluorescence changes) by several seconds and the prolongation of the signal by several minutes. While many functional assays for calcium signaling are termed "flash" assays because they are instantaneous and transient (complete within a few seconds of the stimulus) the addition of the delay reagent, BAPTA-AM, allows the signal to be read by instruments without simultaneous liquid handling.

Figure 2:
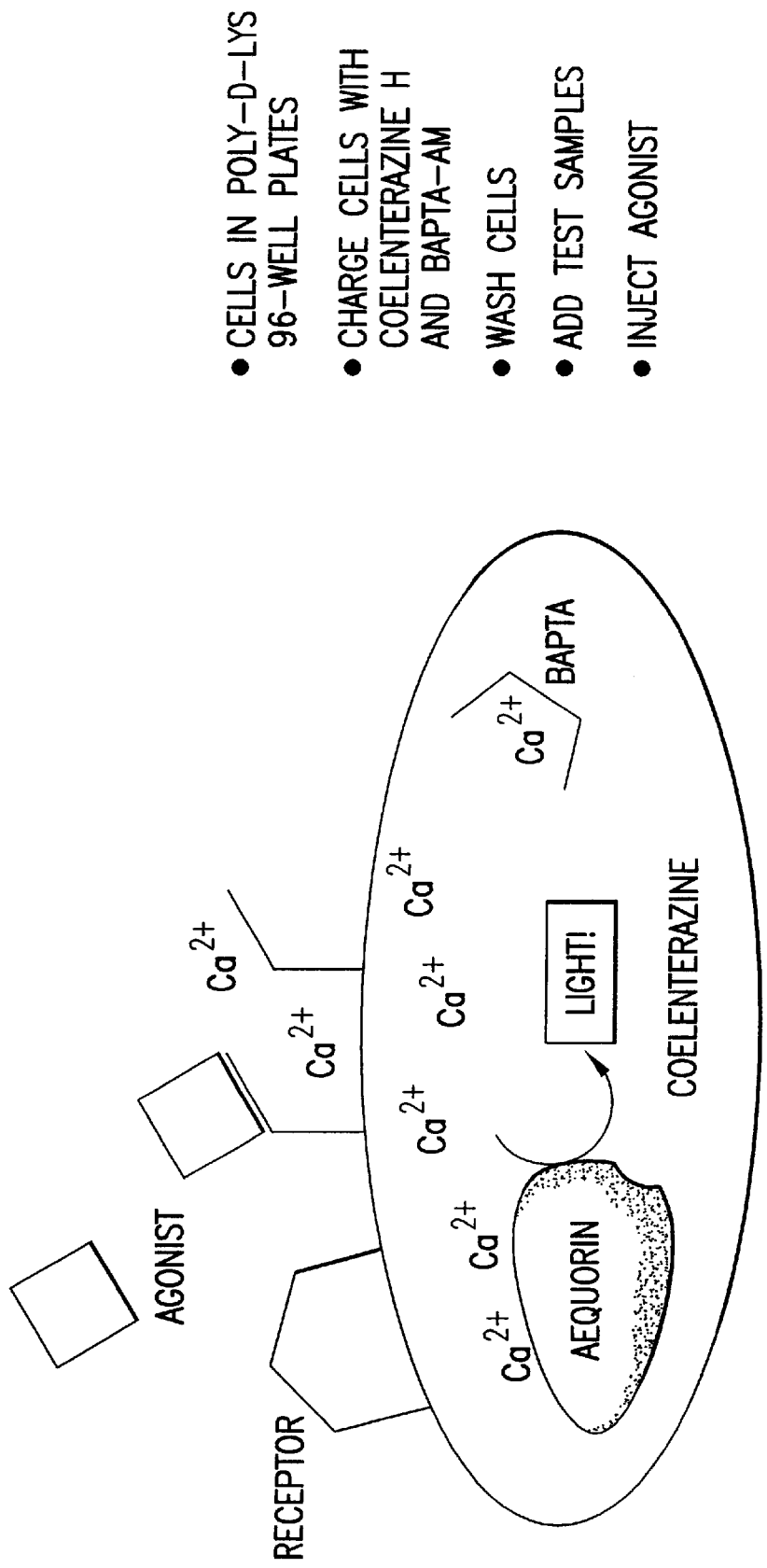
FIG. 2 shows schematic representation of the cell-based functional luminescence assay with intracellular chelator in an assay using an ion channel coexpressed with apoaequorin.

A model for how calcium chelation by BAPTA could delay aequorin luminescence can be discussed with reference to FIG. 2. BAPTA-AM is used to load the calcium chelator BAPTA into cells prior to stimulation. Increases in intracellular calcium, such as occurs when capsaicin binds to the VR1 receptor, will cause aequorin to oxidize coelenterazine to coelenteramide with concomitant release of photons. Light emission could be prevented if a calcium chelator such as BAPTA binds free calcium more rapidly then aequorin. The relative binding rates would then determine the amount of calcium which binds to aequorin (or other calcium sensitive reporters) versus BAPTA. The difference in binding rate may depend on many factors such as; inherent association rates, free concentration of calcium and available BAPTA and aequorin. Since BAPTA can be loaded into cells at concentrations at least 10-fold greater than its affinity for calcium, its capacity for chelating intracellular calcium influx is likely to be determined by the free BAPTA concentration achieved within the cytoplasm, not the free calcium concentration. As free BAPTA becomes bound with calcium, further calcium influx would primarily result in aequorin luminescence. Inactivation of the VR1 receptor, as well as other calcium buffering within the cell, will eventually slow the calcium influx. The luminescence can then be extended as the BAPTA and other cell buffering capacity slowly release calcium back into the cytoplasm of the cell until the calcium returns to resting levels or the aequorin is exhausted.

This invention provides for protocols that delay the calcium response as measured by calcium-sensitive reporters by the use of a cell permeable calcium chelator, for example, BAPTA-AM. These protocols are useful for both fluorescent and luminescent calcium-sensitive reporters. For example, the calcium signal caused by activation of a ligand-gated calcium channel in an aequorin-expressing cell line can be delayed by several seconds and the response extended for several minutes with BAPTA without significantly reducing the total signal output. This means that the fast and transient calcium signals which previously required instrumentation that simultaneously injects and measures these signal can now be performed by a host of other instruments. The methods of this invention can be advantageously applied to whole-cell functional assays of both a calcium ion channel and a G-protein-coupled receptor. In both cases the delay of the fluorescent or luminescence signals are sufficient enough for simultaneous addition of agonist to multiple wells by an external liquid handling system followed by rapid transfer into fluorescent or luminescence imaging systems, for example, the PE BIOSYSTEMS NORTHSTAR™ HTS Workstation.

Glow luminescence assays have been readily adopted into high throughput screening facilities because of their intrinsically high sensitivities and long-lived signals. The signals for chemiluminescence systems such as luciferase and β-galactosidase reporter genes or for alkaline phosphatase conjugates are often stable for several hours. Flash luminescence assays have received less attention for primary screening than glow assays and have been relegated to a more secondary screening role. Increasingly, however there is a need to evaluate the activity of large chemical libraries in whole-cell functional assays that can be performed in a high throughput screening format.

An example of a flash luminescence-based functional assay is the measurement of calcium signaling pathways in cells containing the bioluminescent protein, aequorin (Button, D., and Brownstein, M. (1993) Aequorin-expressing mammalian cell lines used to report $Ca^{2+}$ mobilization. *Cell Calcium* 14, 663–671). Aequorin is a calcium-dependent enzyme that produces light (466 nm) upon oxidation of coelenterazine. Typically, aequorin-based functional cellular assays for G-protein-coupled receptors (GPCRs) or ligand-gated calcium channels are initiated by addition of agonist which increases the intracellular concentration of calcium from intracellular stores or intake of external calcium. The increase of intracellular calcium concentration initiates the reaction of aequorin with its substrate giving rise to a rapid luminescence signal. The kinetics of this flash luminescence response is demonstrated in FIG. 1 where the luminescent signals for the activation of a ligand-gated calcium channel or GPCR attain their maximal levels in just a few seconds and are complete in less than a minute. Therefore the detection of these signals must be made simultaneously upon addition of the agonist. For assays performed in microtiter plates, this requires a luminometer that has simultaneous liquid injection and sample detection capabilities.

This requirement for simultaneous liquid dispensing and signal detection has limited the application of these calcium transient measurements in HTS screens. A principal advantage of this invention, using a chelator to delay the calcium kinetics, is to enable HTS functional assays without expensive instrumentation. With the introduction of FLIPR (MOLECULAR DEVICES)(Sullivan, E., Tucker, E. M., and Dale, I. L. (1999) Measurement of [$Ca^{2+}$] using the fluorometric imaging plate reader (FLIPR). *Calcium Signaling Protocols* 114, 125–133), it is now at least possible to record fluorescence from 96 and 384-well plates with simultaneous liquid addition, but this is an expensive instrument that is not generally accessible. There are currently no equivalent instruments for measuring luminescence.

Several commercial luminescence and fluorescence detectors are available that can simultaneously inject liquid into single or multiple wells such as the WALLAC VICTOR2 (single well), MICROBETA® JET (six wells), or AURORA VIPR (eight wells). Typically, these instruments require 12 to 96 minutes to read a 96-well plate in flash luminescence or fluorescence mode (1 min/well)—rather a long time for most high throughput screening applications. An alternative method is to inject the stimulant/agonist into all sample wells at the same time and measure the luminescence in the whole plate by imaging with a CCD camera, similar to the way that calcium responses are read by calcium-sensitive fluorescent dyes in the FLIPR or FLIPR-384 instruments. Other luminescence or fluorescence imaging systems with integrated liquid handling are expected from other commercial suppliers such as the second generation LEADSEEKER from AMERSHAM, the WALLAC VIEWLUX™ ultraHTS microplate imager, and the MOLECULAR DEVICES CLIPR imager.

Recently, PE BIOSYSTEMS TROPIX introduced a CCD-based luminometer, the NORTHSTAR™ HTS Workstation. This instrument does not have simultaneous liquid dispensing capability but is able to rapidly dispense liquid into 96-well or 384-well microtiter plates by an external 8 or 16-head dispenser and then can quickly transfer the plate to a CCD camera that images the whole plate. The total time for dispensing liquid into a plate and transferring it into the reader can take 10 seconds or more, not fast enough for many flash assays which are complete within 5–10 seconds. Integration of liquid handling systems to detection systems would also be expected to inherently require processing times between liquid dispensing and plate transfer or 10 seconds or greater. The present invention demonstrates the utility of an intracellular calcium chelating agent to delay and/or prolong the calcium signaling response sufficiently to be measured by instrumentation without simultaneous liquid dispensing capability such as the NORTHSTAR™ HTS Workstation.

The effectiveness of the present invention is demonstrated in a model aequorin-based functional cellular assay for a ligand-gated calcium channel. For this assay, HEK293 cells co-expressing the receptor of interest and apoaequorin were grown to confluence in BIOCOAT poly-D-lysine opaque white 96-well microtiter plates (BECTON DICKINSON). The cells were maintained on a standard growth media. The cells were charged with growth media supplemented with 5 uM of coelenterazine h (MOLECULAR PROBES, Eugene, Oreg.) for 2 hr at 37° C. in a humidified incubator at 5% $CO_2$. The charged cells were then washed and loaded with assay buffer.

Addition of agonist caused the rapid and transient luminescent signal that was complete within 10–15 seconds (FIG. 1). The kinetics of the flash luminescent signal was followed by using a WALLAC MICROBETA JET instrument where agonist was injected directly into the wells containing the charged cells. As a buffering reagent the cell permeable acetoxymethyl ester BAPTA-AM was used. BAPTA is a specific calcium chelator that rapidly binds and releases calcium. Addition of BAPTA-AM to the cells was equally effective by either including the chelator during the charging of the cells with coelenterazine or by a subsequent incubation in growth media for 1 hr at 37° C. and 5% $CO_2$. A schematic representation of this assay appears in FIG. 2.

Figure 3:
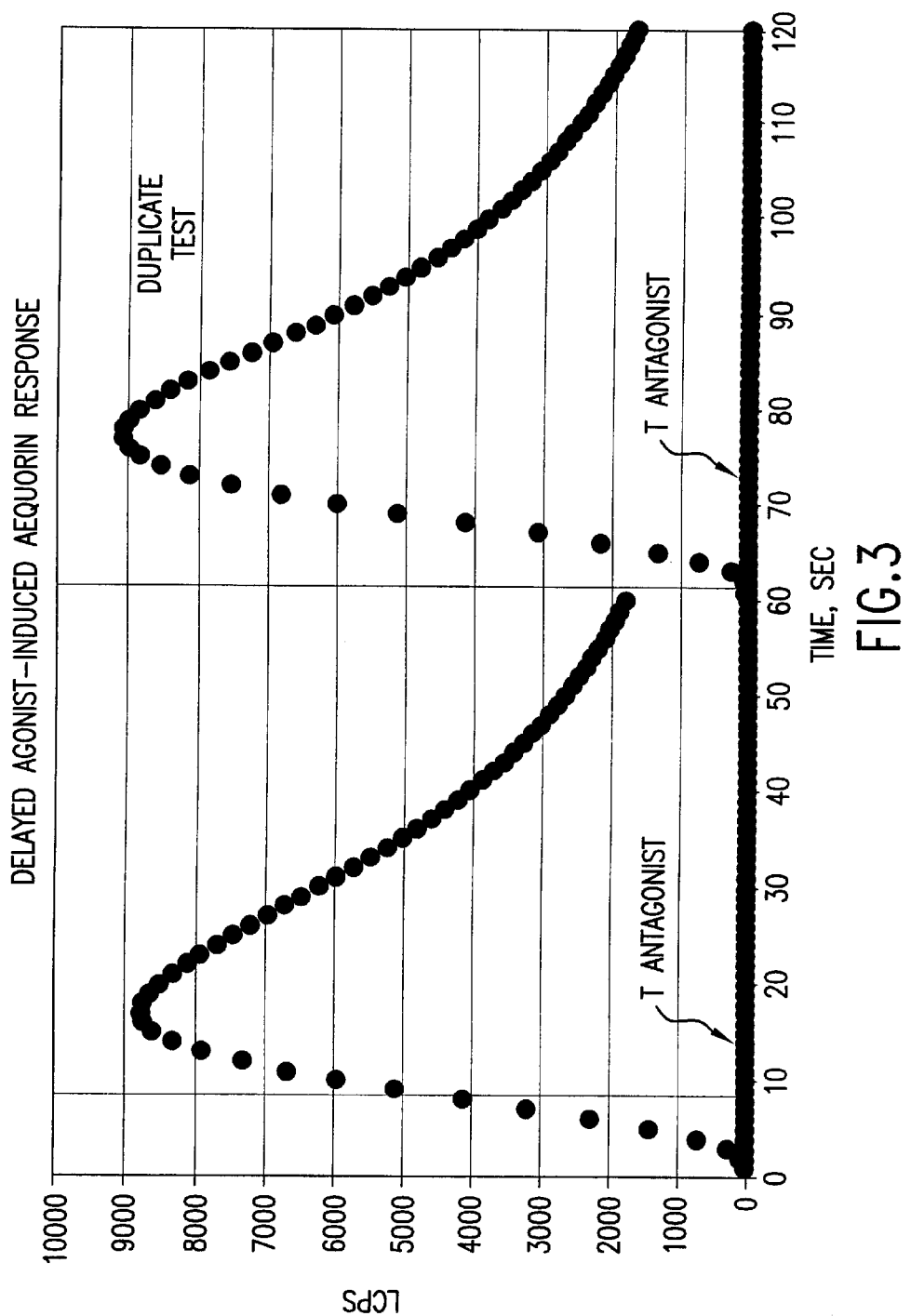
FIG. 3 shows effect of a receptor antagonist on the kinetics of the luminescence upon the addition of an intracellular chelator in an assay using an ion channel coexpressed with apoaequorin.

The addition of increasing levels of BAPTA-AM (0–30 uM) caused an initial delay in the aequorin-based luminescence signal upon injection of agonist and extended the signal far greater than 30 seconds (FIG. 1). The addition of a known receptor antagonist was able to completely block the signal (FIG. 3). Subsequent addition of lysis buffer (0.1% triton X100) demonstrated that the decrease in signal was attributable to competitive blocking of the receptor-mediated calcium signal by the antagonist. While the kinetics of the aequorin-response was altered by buffering with BAPTA, the overall signal was not significantly suppressed.

Figure 4:
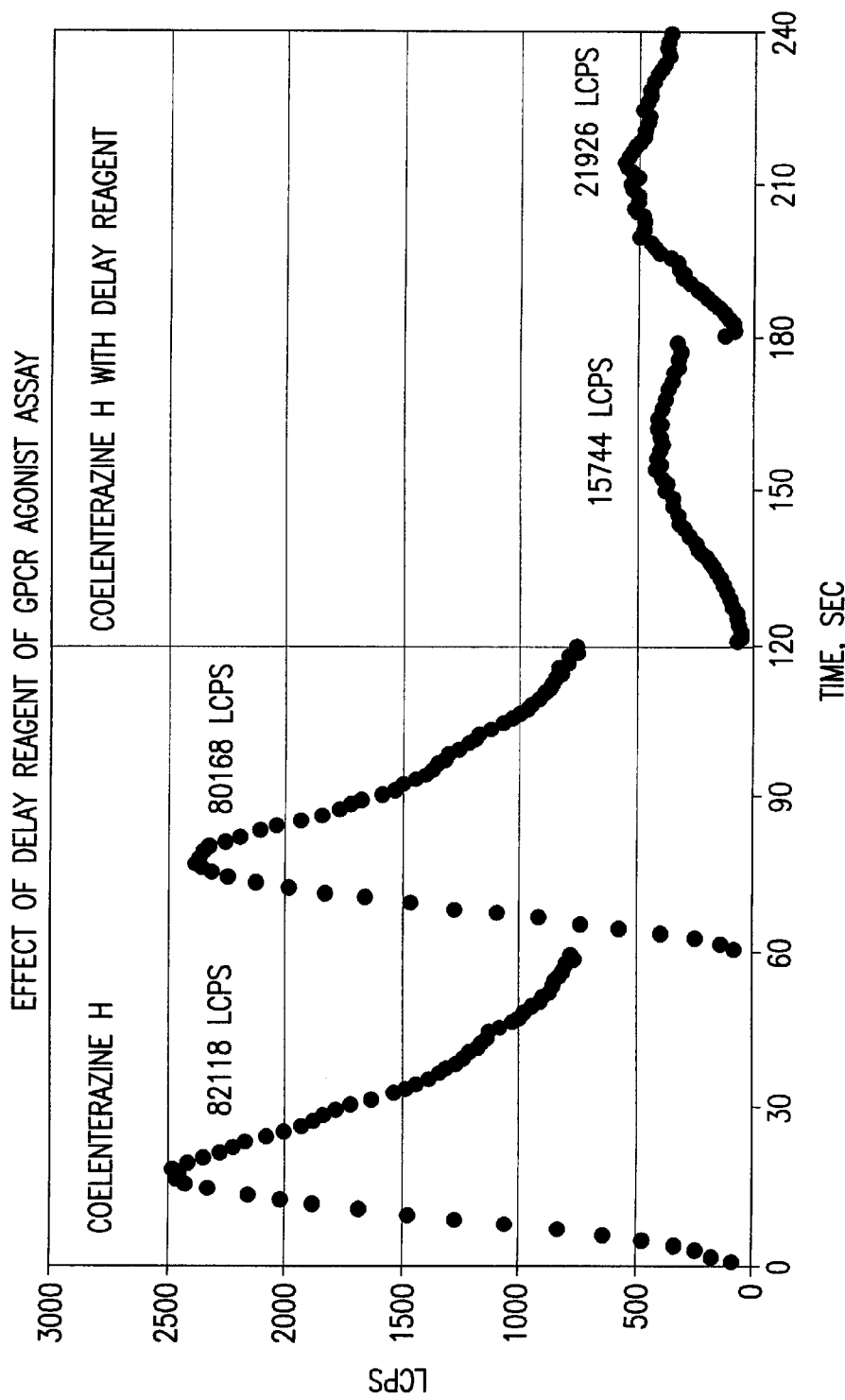
FIG. 4 shows the kinetics plus or minus the intracellular calcium chelator in an assay using a GPCR coexpressed with apoaequorin.
Figure 5:
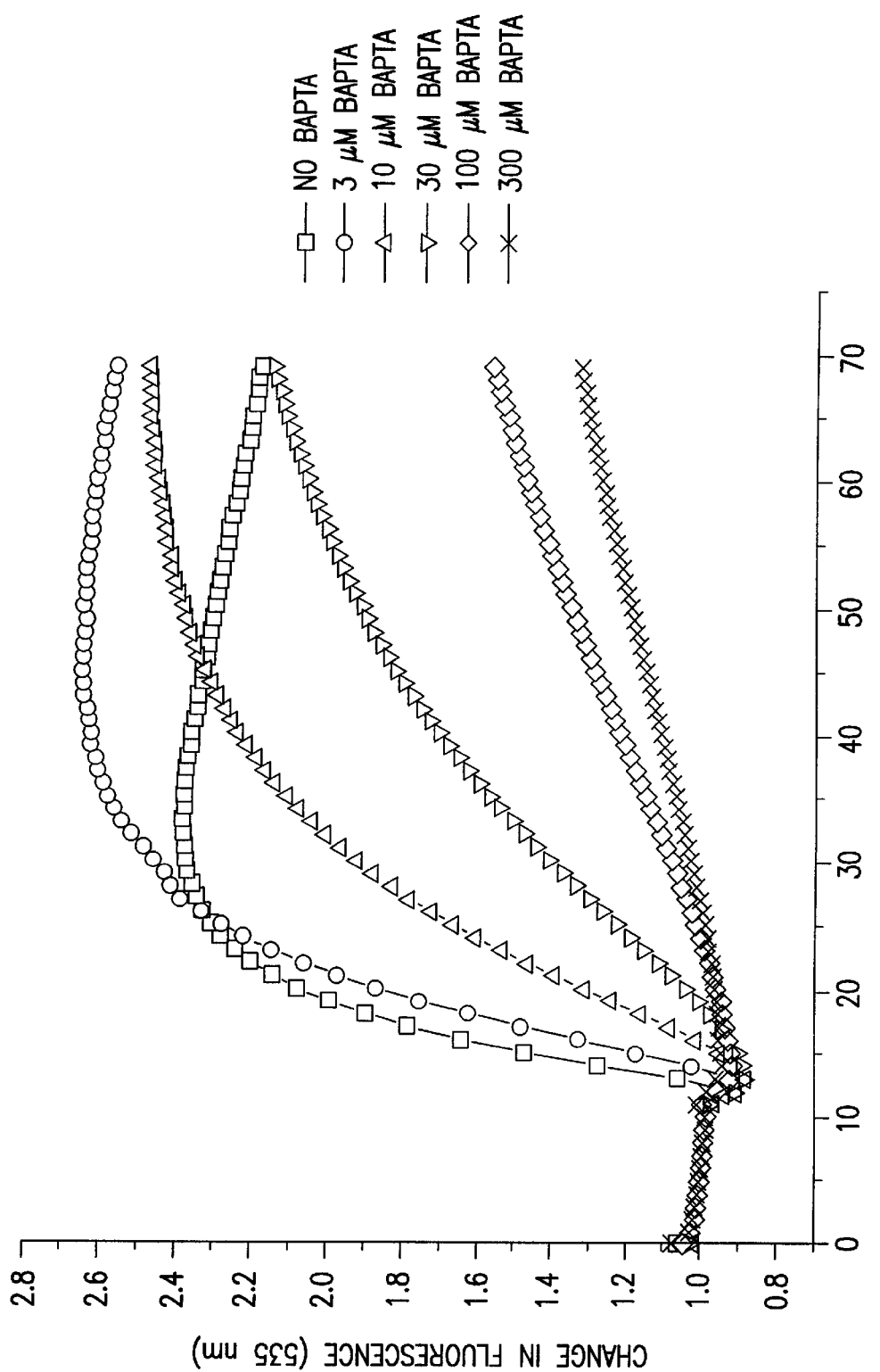
FIG. 5 shows the kinetics of the calcium dependent fluorescence upon the addition of an intracellular chelator in an assay using a ion channel.

To demonstrate the generic utility of such a delay reagent for calcium signaling, the exemplary chelator BAPTA-AM was tested in a functional aequorin-based cellular assay for a G-protein coupled receptor (GPCR). As with the ligand-gated calcium ion channel, HEK293 cells co-expressing the GPCR of interest and apoaequorin were grown to confluence on poly-D-lysine coated plates and charged with coelenterazine. Addition of BAPTA-AM also altered the kinetics of the calcium signal following stimulation with agonist through the release of calcium from intracellular stores by the G-protein pathway (FIG. 4). Further demonstration of the generic utility of the delay reagent was accomplished when the fluorescence of a calcium sensitive dye (Fluo 3, Fluo 4; FIG. 5) was substituted for the luminescence generated from the aequorin-response in order to detect the fluctuation of intracellular calcium concentration upon addition of agonist to HEK-293 cells expressing a calcium ion channel.

While BAPTA-AM was chosen to demonstrate the potential of using an intracellular chelator in buffering the calcium signaling in cells, other calcium binding reagents can be useful. These include other structurally related chelators such as fura-2 or other fluorescent dyes, or photoactivated chelators such as diazo-2, and their cell permeable derivatives. Alternatively, calcium-binding proteins such as modified aequorins or calmodulin-GFP chimers might substitute for BAPTA as constitutive delay reagents (Tsien, R. Y. (1980) New calcium indicators and buffers with high selectivity against magnesium and protons: design, synthesis, and properties of prototype structures. *Biochemistry* 19, 2396–2404; Gonzalez, J. E., Oades, K., Leychis, Y. Harootunian, A., and Negulescu, P. (1999) Cell-based assays and instrumentation for screening ion-channel targets. *Drug Discovery Today* 4, 431–439; Ungrin, M. D., Singh, L. M. R., Stocco, R., Sas, D. E., Abramovitz, M. (1999) An automated aequorin luminescence-based functional calcium assay for G-protein-coupled receptors. *Anal. Biochem.* 272, 34–42).

Any number of these reagents have the potential of being useful as delay reagents for the aequorin-based functional assays. One of skill in the art need only try any particular reagent in the assay taught herein and compare the results to those obtained using BAPTA-AM. These reagents might also be generically useful as delay reagents for functional assays using calcium signaling in general, not just from the aequorin-based bioluminescence reporter assay.

It is also noticed that addition of a specific receptor antagonist can affect the kinetics of the observed calcium transient. For some applications the use of an antagonist might be sufficient for altering the kinetics of the functional assay. Indeed, several commercial products have been introduced that extend flash fluorescence and luminescence to a "glow" format. The PACKARD LUCLITE® assay kit is an example of an assay method that utilize a specific luciferase inhibitor to delay the kinetics of a luminescence signal from a few minutes to several hours.

Assays

Assays of the present invention can be designed in many formats generally known in the art of screening compounds for biological activity or for binding to receptors. Assays of the present invention can advantageously exploit the ability of intracellular chelators of divalent cations to buffer the kinetics of signal generation triggered by the accumulation of divalent cations.

The invention is advantageously employed in whole cell functional assays and high throughput screening assays for calcium signaling such as calcium channels and GPCR's to extend the signal so that it could be read by conventional plate readers. The present invention can be applied generally to whole cell functional assays for any calcium channel, or any receptor or ion channel that is coupled to a calcium channel. For example, one can apply the present invention to an assay of a receptor that is coupled to a voltage-gated calcium channel. However, for clarity in the description of the application of the invention, we generally refer to either a calcium channel or a receptor.

The delay reagent may have utility for practitioners who need to examine calcium signaling in cells but do not have instrumentation to perform simultaneous injection and measurement of the fast and transient signal. The delay provided in assays of the present invention is particularly useful for high throughput screening of whole cell functional assays where 96-well, 384-well, 3456-well or other plate formats are used. Here the delay of the calcium triggered signal generation provides for the addition of reagents and handling of plates over an extended time-frame as is more amenable to these plate densities. One can employ the intracellular chelators in any assay providing a functional readout where additional time afforded by the delay would allow additional manipulation of the cells such as addition of other reagents or transfer of sample, or if a kinetic equilibrium needs to be established.

The present invention includes methods of identifying compounds that specifically interact with receptor polypeptides. Compounds that interact with a receptor can stimulate or inhibit the activity of a receptor. The specificity of binding of compounds having affinity for a receptor can be shown by measuring the affinity of the compounds to membranes from recombinant cells expressing a receptor polypeptide. Expression of receptor polypeptides and screening for compounds that bind to a receptor or that inhibit the activation of a receptor, provides an effective method for the rapid selection of compounds with affinity for a receptor.

Therefore, the present invention includes assays by which compounds that are receptor agonists, antagonists, and inhibitors may be identified. The assay methods of the present invention differ from those described in the art because the present assays incorporate at least one step wherein the cells are contacted with an intracellular chelator.

The present invention is broadly applicable to assay formats known in the art. The present invention advantageously provides for the use of instrumentation to detect fluorescent or luminescent signals from cells without the requirement for simultaneous liquid handling at the time of detection. General methods and assay formats for identifying ligands, agonists and antagonists are well known in the art and can be adapted to identify agonists and antagonists of receptors expressed in cells that are contacted with an intracellular chelator before or during an assay. The order of steps in any given method can be varied or performed concurrently as will be recognized by those of skill in the art of assays. The following is a sampling of the variety of formats that can be used to conduct an assay of the present invention.

Cells useful in the present invention contain a calcium sensitive reporter system. In some embodiments, the cell is engineered to express the reporter system from stably integrated genes. Alternatively, the cells can be transiently transfected with nucleic acids encoding a calcium sensitive reporter. Most commonly, the reporter system consists of a protein expressed in the cell, for example, an apo-aequorin or a green fluorescent protein-calmodulin chimer. However, it is conceivable that a multiprotein system, or multipolypeptide assembly that is sensitive to and generates a signal in response to calcium can be used. Alternatively, one can use a non-proteinaceous organic compound, including the calcium sensitive dyes noted herein. Cell membrane permeable dyes are preferred. Dyes can be trapped inside cells by contacting cells with derivatized ester or amide dyes. After uptake of the dye the amide or ester is cleaved trapping the dye moiety within the cell (Tsien, R. Y. (1981) A non-disruptive technique for loading calcium buffers and indicators into cells. *Nature* 290, 527–528).

Accordingly, the present invention includes a method for determining whether a candidate compound is an inhibitor of a receptor using cells that contain a calcium sensitive reporter such as apo-aequorin or a green fluorescent protein-calmodulin chimer, the method of which comprises:

(a) transfecting cells with an expression vector encoding a receptor polypeptide;

(b) allowing the transfected cells to grow for a time sufficient to allow receptor to be expressed in the cells;

(c) exposing the cells to an intracellular chelator of calcium;

(d) exposing the cells to an activator of the receptor in the presence and in the absence of the compound;

(e) measuring the signal generated in the of cells; and (f) comparing the amount of signal in the presence and the absence of the compound where a decrease in the amount of signal in the presence of the compound indicates that the compound is an inhibitor of the activation of the receptor.

Accordingly, the present invention also includes a method for determining whether a candidate compound is an agonist of a receptor using cells that contain a calcium sensitive reporter such as apo-aequorin or a green fluorescent protein-calmodulin chimer, the method of which comprises:

(a) transfecting cells with an expression vector encoding a receptor polypeptide;

(b) allowing the transfected cells to grow for a time sufficient to allow receptor to be expressed in the cells;

(c) exposing the cells to an intracellular chelator of calcium;

(d) exposing the cells to a test compound;

(e) measuring the signal generated in the cells; and (f) comparing the amount of signal in the presence and the absence of the compound where an increase in signal similar to a known agonist indicates that the compound is an agonist of the receptor. An increase in signal more than a buffer control but less than a known agonist indicates the compound is a partial agonist.

The conditions under which step (d) of the method is practiced are conditions that are typically used in the art for the study of protein-ligand interactions: e.g., physiological pH; salt conditions such as those represented by such commonly used buffers as PBS or in tissue culture media; a temperature of about 4° C. to about 55° C. In this step the receptor and candidate compound can be applied to the cell sequentially or concurrently. It is preferred that the candidate compound is applied first or that the compound and receptor are applied concurrently.

In an alternative embodiment of the general assays described above, the cells lack an endogenous calcium sensitive reporter system and are transiently transfected with the system for purposes of conducting the assay. This embodiment can be useful with cells that endogenously express or are stably transfected with a receptor one desires to use in the assay. An additional embodiment would be to use a calcium-sensitive fluorescent dye, such as Fluo-3 instead of an endogenous calcium sensitive reporter system. In this embodiment an additional step between (b) and (c) would be added where the cells are incubated with 1–10 $\mu$M Fluo-3 AM, a membrane permeant ester of Fluo-3. A further embodiment to the general assay formats would be to eliminate steps (a) and (b) and start instead with cells that stably express the receptor polypeptide.

As a further modification of the above-described methods, RNA encoding receptor can be prepared as, e.g., by in vitro transcription using a plasmid containing receptor under the control of a bacteriophage T7 promoter, and the RNA can be microinjected into Xenopus oocytes in order to cause the expression of receptor in the oocytes. The oocytes are then exposed to an intracellular chelator. Compounds are then tested for binding to the receptor or inhibition of activation of receptor expressed in the oocytes. As in all assays of this invention, a step where the cells are exposed to an intracellular chelator is incorporated into the assay.

The above whole cell methods can be used in assays where one desires to assess whether a compound can interact with receptor.

EXAMPLE 1

Cell Lines and Growth Conditions

Parental HEK293 cell lines expressing apoaequorin (293AEQ17 cells) (Button, D., and Brownstein, M. (1993) Aequorin-expressing mammalian cell lines used to report $Ca^{2+}$ mobilization. *Cell Calcium* 14, 663–671) were used to develop stable clonal cell lines expressing a ligand-gated calcium ion channel or GPCR. The ion channel 293AEQ17 cells were maintained on growth media containing DMEM (GIBCOBRL, high glucose, with L-glutamine, with 110 mg/L sodium pyruvate, with pyridoxine HCl), 25 mM HEPES (GIBCOBRL, 1M stock), 0.5 mg/mL geneticin (GIBCOBRL, 50 mg/mL stock), 1 $\mu$g/mL puromycin (CLONTECH), and 10% fetal bovine serum (Gemini Bio-Products, heat inactivated) at 37° C., 5% $CO_2$. The GPCR 293AEQ17 cells were maintained on growth media containing DMEM (GIBCOBRL, high glucose, with L-glutamine, with 110 mg/L sodium pyruvate, with pyridoxine HCl), 25 mM HEPES, 0.5 mg/mL geneticin, 0.2 mg/mL hygromycin (BOEHRINGER MANHEIM), and 10% fetal bovine serum (HYCLONE, defined) at 37° C., 5% $CO_2$.

Plating and Charging of Cells.

Cells were grown to confluence in tissue culture flasks (T-225, CORNING) and harvested by trypsinization (Trypsin/EDTA, GIBCOBRL). Cells were dispensed (about $1 \times 10^5$ cells/0.2 mL/well) into 96-well white opaque or clear-bottom BIOCOAT poly-D-lysine plates (BECTON DICKINSON, Bedford, Mass.) in growth media and incubated overnight at 37° C. in a humidified incubator at 5% $CO_2$. For charging the cells with coelenterazine, the growth media was removed by aspiration using a TITERTEK cell washer, followed by addition of growth media (DMEM media with 0.1% fetal bovine serum and 0.15 mM reduced glutathione) supplemented with 5 $\mu$M coelenterazine h (MOLECULAR PROBES, Eugene, Oreg.). For some experiments other coelenterazine analogs were substituted in the charge buffer as indicated. The cells were further incubated in charge buffer for 2 hours at 37° C. in a humidified incubator at 5% $CO^2$. The media was then removed and the cells were washed with Dulbecco's phosphate-buffered saline with calcium and magnesium (PBS, GIBCOBRL) containing 10 mM HEPES and 2 mg/mL glucose) supplemented with 0–30 uM of 1,2-bis(o-aminophenoxy)ethane-N,N,N',N'-tetraacetic acid tetra (acetoxymethyl) ester (BAPTA-AM, MOLECULAR PROBES) and 0.02% Pluronic F-127 solution (MOLECULAR PROBES) and incubated for 1 hour at 37° C. in a humidified incubator at 5% $CO^2$. Alternatively, cells were charged at the same time with coelenterazine h and BAPTA-AM for 2 hours at 37° C. in a humidified incubator at 5% $CO^2$. The cells were then washed and loaded with 90 uL of PBS supplemented with 10 mM HEPES and 2 mg/mL glucose. Antagonist or DMSO controls were added to wells (10 uL, 1% DMSO final).

The potential buffering or delay of the aequorin-based luminescence was evaluated in a functional cellular assay for a ligand-gated calcium channel. We found that low levels of BAPTA were able to alter the kinetics of the luminescence signal upon addition of agonist without significantly suppressing the total accumulated light as observed for addition of low levels of antagonist (FIGS. 1–4).

EXAMPLE 2

Measurement of Fluorescence with VR1 cells

Cell Lines and Growth Conditions

Parental HEK293 cell lines expressing apoaequorin (293AEQ17 cells) were used to develop stable clonal cell lines expressing the rat VR1 capsaicin receptor (Caterina, M. J., Schumacher, M. A., Tominaga, M., Rosen, T. A., Levine, J. D., and Julius, D. (1997) The capsaicin receptor: a heat-activated ion channel in the pain pathway. *Nature* 389, 816–824). The VR1 293AEQ17 were maintained on growth media containing DMEM (GIBCOBRL, high glucose, with L-glutamine, with 110 mg/L sodium pyruvate, with pyridoxine HCl), 25 mM HEPES (GIBCOBRL, 1M stock), 0.5 mg/mL geneticin (GIBCOBRL, 50 mg/mL stock), 1 μg/mL puromycin (CLONTECH), and 10% fetal bovine serum (GEMINI BIO-PRODUCTS, heat inactivated) at 37° C., 10% $CO^2$.

Preparation of Cells for Assay

Cells were grown to 80–95% confluence in tissue culture flasks (T-225, CORNING) and harvested by trypsinization (Trypsin/EDTA, GIBCOBRL). Cells were dispensed (about $1 \times 10^5$ cells/0.2 ml/well) into 96-well black clear-bottom BIOCOAT poly-D-lysine plates (BECTON DICKENSON, Bedford, Mass.) in growth media and incubated overnight at 37° C. in a humidified incubator at 10% $CO^2$. Cells were washed once with 200 μls of enriched PBS (Dulbecco's PBS (GIBCOBRL #14040-117), 10 mM HEPES, 2 g/L glucose; pH 7.2) and then incubated with 100 μl of 5 μM fluo-3-AM (MOLECULAR PROBES #F1241) with or without of 1,2-bis(o-aminophenoxy)ethane-N,N,N',N'-tetraacetic acid tetra (acetoxymethyl) ester (BAPTA-AM, MOLECULAR PROBES #B 1205) in enriched PBS containing 0.02% pluronic F-127 (MOLECULAR PROBES #P-3000) for 30–70 minutes. Wells were washed two times with 100 μl of enriched-PBS, and then 100 μl enriched-PBS with or without antagonist was added for 15–30 minutes prior to assay on the AURORA fluorescence plate reader VIPR (ex. 480 nm, em. 535 nm). The BAPTA-AM can be incubated 30 minutes as a separate step after fluo-3 staining and prior to drug addition, with no appreciable differences in signal. The calcium response was initiated by addition of 100 μl of the indicated concentration of capsaicin (SIGMA #M2028). The VIPR instrument was used to add agonist (in 100 μl enriched-PBS) after recording a 10 sec. baseline and the fluorescence was measured for up to 300 sec.

Figure 6A:
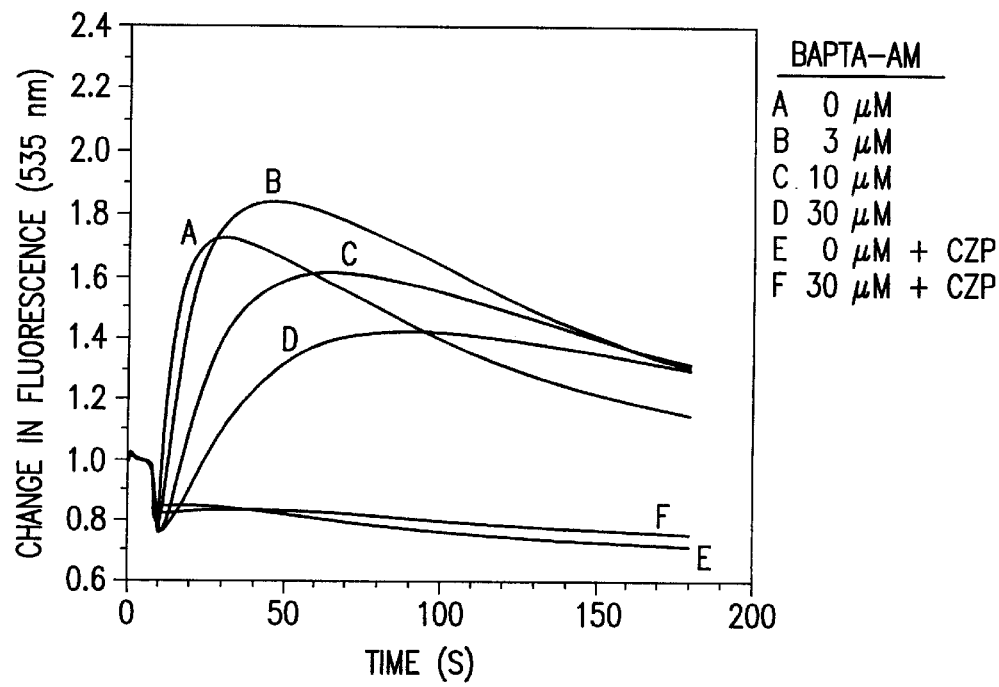
FIGS. 6(A and B) shows that BAPTA delays the calcium response in VR1 cells as measured by fluo-3 fluorescence. VR1 cells were grown in 96-well assay plates overnight and then loaded with 5 $\mu$M fluo-3-AM for 30 minutes, in the absence or presence of the indicated concentration of BAPTA-AM as described in Materials and Methods. The cells were washed and either PBS or 20 $\mu$M capsazepine was added for 30 minutes. The plate was then read on a VIPR fluorescence detector (ex.480 nm; em. 535 nm; Gonzalez, J. E., Oades, K., Leychis, Y. Harootunian, A., and Negulescu, P. (1999) Cell-based assays and instrumentation for screening ion-channel targets. *Drug Discovery Today* 4, 431–439) which added 0.5 $\mu$M (A) or 0.1 $\mu$M (B) capsaicin after reading for 8 s, and continued recording for a total of 180s. The data were acquired at 1 Hz and all data were normalized to the initial baseline fluorescence (2–5 s). The data shown are the average from four identical wells.

Changes in intracellular calcium were measured using the fluo-3 dye and detecting the kinetics of the response after addition of the VR1 agonist, capsaicin (0.5 uM) to cells expressing VR1 using a VIPR fluorescence plate reader (FIGS. 5 & 6A). In the absence of BAPTA, the response peaked in about 20 sec and decayed to 50% in about 150 sec. This response was completely blocked by 20 μM capsazepine, a selective competitive antagonist of VR1. Incubation of the cells for 30 minutes with 3 μM BAPTA-AM resulted in a delay of the fluorescence signal with a peak at about 40 sec, but the fluo-3 signal decay time (≈150s) was unaffected. However, increasing the concentration of BAPTA-AM to 10 and 30 μM caused a significant delay in the peak response time of up to 100 sec, with a sustained fluorescence signal that displayed no significant decay on this time scale (3 minutes). It is worth noting that the fluorescence only partially decayed after the 3 minutes, even in the absence of BAPTA-AM, and this decay may be due, in part, to photobleaching of fluo-3.

Figure 6B:
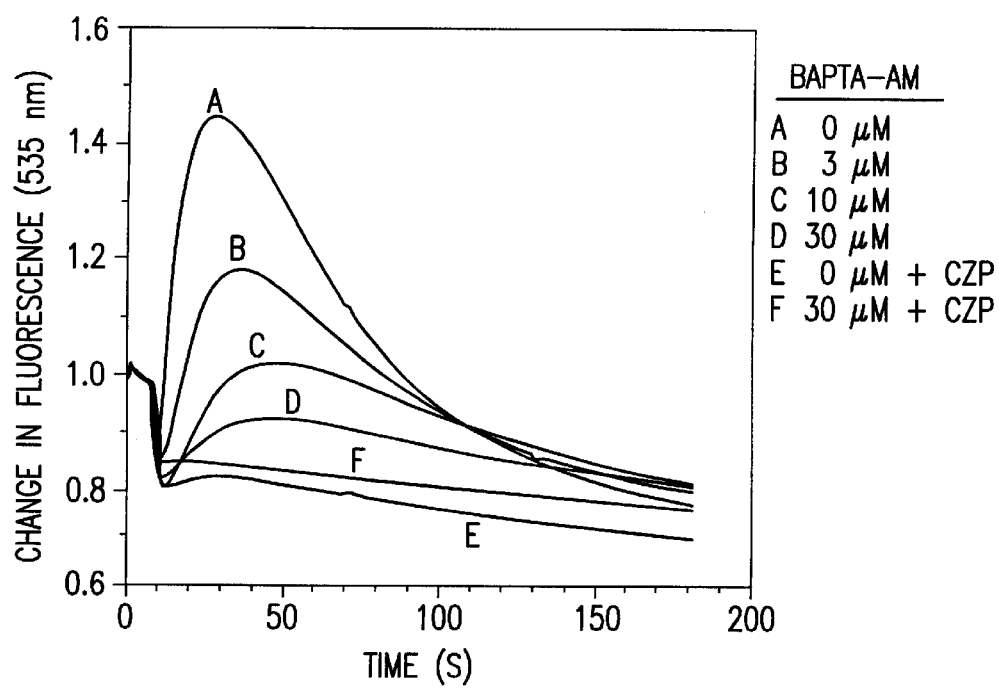

It was important to use the correct balance between the extent of agonist activation and calcium chelation by BAPTA. Therefore, titration experiments are useful to establish appropriate parameters. As expected, when a lower agonist concentration was used (FIG. 6B, 0.1 μM capsaicin) there was a decrease in the fluorescence response and it decayed more rapidly. At this low agonist concentration, 3 μM BAPTA decreased the peak signal without a large effect on the time to peak or decay kinetics. At 30 μM chelator, the stable calcium signal is only slightly larger in the absence of antagonist as compared to the presence of 20 μM capsazepine. Yet, even this small fluorescence signal was sustained over 30–180 sec, giving an easily discernible window compared to the decay in the fluorescence signal when blocked by antagonist.

EXAMPLE 3

Measurement of Fluorescence with Cells Expressing Growth Hormone Secretagogue Receptor 1a Cell Lines and Growth Conditions.

Parental HEK293 cell lines expressing apoaequorin (293AEQ17 cells) were used to develop a stable clonal cell line expressing human growth hormone secretagogue receptor type 1a (hGHSRIA, Smith, R. G., Griffin, P. R., Xu, Y., Smith, A. G. A., Liu, K., Calacay, J., Feighner, S. D., Pong., C.-S., Leong, D., Pomes, A., Cheng, K., Van der Ploeg, L. H. T., Howard, A. D., Schaeffer, J., & Leonard, R. J. (2000) Adenosine: A partial agonist of the growth hormone secretagogue receptor. Biochem. Biophys. Res. Commun. 276, 1306–1313; Bednarek, M. A., Feighner, S. C., Pong, S.-S., McKee, K. K., Hreniuk, D. L., Silva, M. V., Warren, V. A., Howard, A. D., Van der Ploeg, L. H. Y., and Heck J. V. (2000) Structure-function studies on the new growth hormone-releasing peptide, ghrelin: Minimal sequence of ghrelin necessary for activation of growth hormone secretagogue receptor 1a. J. Med Chem. 43 4370–4376). The hGHSR1A and parental 293AEQ17 cells were maintained on growth media containing DMEM (GIBCOBRL, high glucose, with L-glutamine, with 110 mg/L sodium pyruvate, with pyridoxine HCl), 25 mM HEPES (GIBCOBRL, 1M stock), 0.5 mg/mL geneticin (GIBCOBRL, 50 mg/mL stock), 0.2 mg/mL hygromycin (BOEHRINGER MANNHEIM), and 10% fetal bovine serum (HYCLONE, defined) at 37° C., 10% $CO^2$.

Preparation of Cells for Assay

Cells were grown to 80–95% confluence in tissue culture flasks (T-225, Corning) and harvested by trypsinization (Trypsin/EDTA, GIBCOBRL). Cells were dispensed (about $1 \times 10^5$ cells/0.2 ml/well) into 96-well black clear-bottom BIOCOAT poly-D-lysine plates (BECTON DICKENSON, Bedford, Mass.) in growth media and incubated overnight at 37° C. in a humidified incubator at 10% $CO^2$. Cells were washed once with 200 μls of enriched PBS (Dulbecco's PBS (GIBCOBRL #14040-117),10 mM HEPES, 2 g/L glucose; pH 7.2) and then incubated with 100 μl of 5 μM fluo-4-AM (#F14202 respectively) with or without of 1,2-bis(o-aminophenoxy)ethane-N,N,N',N'-tetraacetic acid tetra (acetoxymethyl) ester (BAPTA-AM, MOLECULAR PROBES #B1205) in enriched PBS containing 0.02% pluronic F-127 (MOLECULAR PROBES #P-3000) for 30–70 minutes. Wells were washed two times with 100 μl of enriched-PBS, and then 100 μl enriched-PBS with or without antagonist was added for 15–30 minutes prior to assay on the AURORA fluorescence plate reader VIPR (ex. 480 nm, em. 535 nm). The calcium response was initiated by addition of 100 μl of the indicated concentration of ghrelin (PHOENIX PHARMACEUTICALS #031031). The VIPR instrument was used to add agonist (in 100 μl enriched-PBS) after recording a 10 sec. baseline and the fluorescence was measured for up to 300 sec.

Figure 8A:
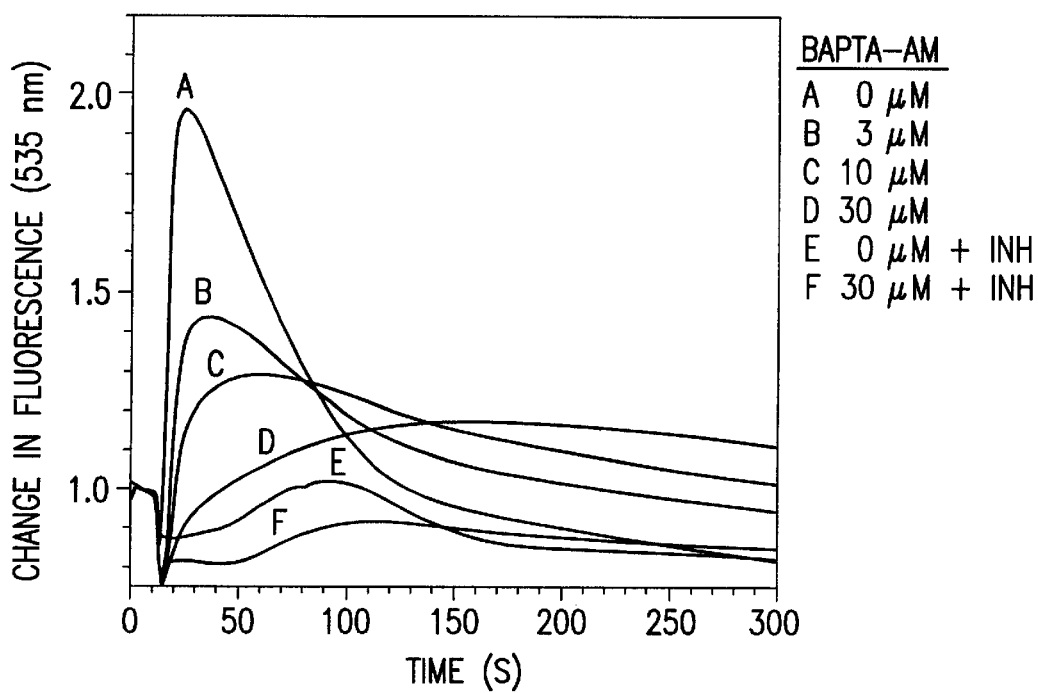
FIGS. 8(A and B) shows that BAPTA delays the calcium response in hGHSR1 as measured by both fluorescence and luminescence. Cells which express hGHSR1A a were grown in 96-well assay plates overnight and then loaded with either (A) 5 $\mu$M fluo-4-AM for 70 minutes as described in FIG. 2 or (B) 5 $\mu$M coelenterazine as described in FIG. 3. The cells were washed with PBS and then incubated with the indicated concentrations of BAPTA-AM for 30 minutes. The cells were washed again with PBS and then incubated with or without 10 $\mu$M L-756,867 for 30 minutes. (A) Fluorescence response on the VIPR (ex.480 nm; em. 535 nm) after addition of 100 nM ghrelin. Data were normalized to the initial baseline fluorescence (2–5 s) and represent the average of 12 or 4 wells in the absence or presence of L-756,867, respectively. (B) aequorin luminescence measured on the WALLAC MICROBETA JET after addition of 100 nM ghrelin. Data are the average of 6 wells and the inset shows the 20 $\mu$M BAPTA-AM data on a different scale with the standard deviation for each 1 sec determination.

The calcium transient activated by the hGHSR1a agonist, ghrelin (100 nM), monitored with fluo-4, was measured using the VIPR (FIG. 8A). The ghrelin induced calcium responses were inhibited by the known GHSR antagonist L-756,867. Activation of hGHSR1a caused a rapid increase in fluorescence that reached a maximum in about 15 sec and completely decayed to baseline level in about 100 seconds. The addition of BAPTA (30 μM BAPTA-AM) delayed the peak fluorescence response from 15 sec to 150 sec, with a stable fluorescent signal for up to 5 minutes.

EXAMPLE 4

Measurement of Fluorescence with Cell Expressing Muscarinic Acetylcholine Receptors Cell Lines and Growth Conditions.

Parental BEK293 cell lines expressing apoaequorin (293AEQ17 cells) were maintained on growth media containing DMEM (GIBCOBRL, high glucose, with L-glutamine, with 110 mg/L sodium pyruvate, with pyridoxine HCl), 25 mM HEPES (GIBCOBRL, 1 M stock), 0.5 mg/mL geneticin (GIBCOBRL, 50 mg/mL stock), and 10% fetal bovine serum (GEMINI BIO-PRODUCTS, heat inactivated) at 37° C., 10% $CO^2$.

Preparation of Cells for Assay

Cells were grown to 80–95% confluence in tissue culture flasks (T-225, Corning) and harvested by trypsinization (Trypsin/EDTA, GIBCOBRL). Cells were dispensed (about $1 \times 10^5$ cells/0.2 ml/well) into 96-well black clear-bottom BIOCOAT poly-D-lysine plates (BECTON DICKENSON, Bedford, Mass.) in growth media and incubated overnight at 37° C. in a humidified incubator at 10% $CO^2$. Cells were washed once with 200 μls of enriched PBS (Dulbecco's PBS (GIBCOBRL #14040-117), 10 mM HEPES, 2 g/L glucose; pH 7.2) and then incubated with 100 μl of 5 μM fluo-4-AM (MOLECULAR PROBES #F14202) with or without of 1,2-bis(o-aminophenoxy)ethane-N,N,N',N'-tetraacetic acid tetra(acetoxymethyl) ester (BAPTA-AM, MOLECULAR PROBES #B1205) in enriched PBS containing 0.02% pluronic F-127 (MOLECULAR PROBES #P-3000) for 30–70 minutes. Wells were washed two times with 100 μl of enriched-PBS, and then 100 μl enriched-PBS with or without antagonist was added for 15–30 minutes prior to assay on the AURORA fluorescence plate reader VIPR (ex. 480 nm, em. 535 nm). The calcium response was initiated by addition of 100 μl of the indicated concentration of (+/−)-muscarine (SIGMA #M0405). The VIPR instrument was used to add agonist (in 100 μl enriched-PBS) after recording a 10 sec. baseline and the fluorescence was measured for up to 300 sec.

Figure 9A:
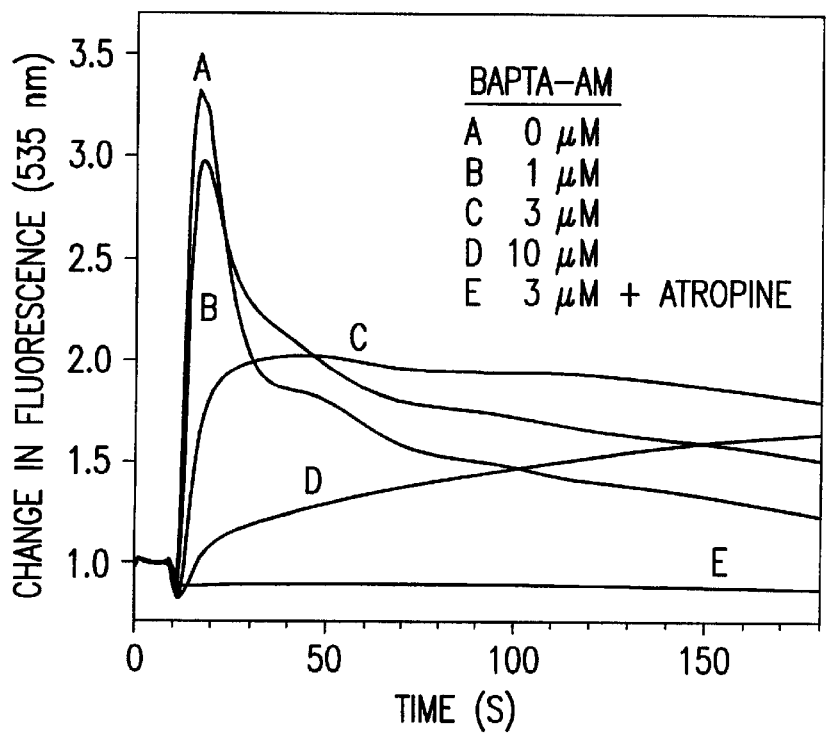
FIGS. 9(A and B) shows that BAPTA delays the calcium response in HEK-AEQ cells as measured by fluo-4 fluorescence. The HEK-AEQ cells have an endogenous mAChR that is coupled to InsP$_3$ mediated release of calcium from intracellular stores. (A) Cells were grown overnight in 96-well assay plates and then incubated for 60 minutes with 5 $\mu$M fluo-4-AM +/− the indicated concentration of BAPTA-AM. Cells were washed with PBS and had either PBS or 50 $\mu$M atropine added for 15 minutes. The plate was then read on a VIPR fluorescence detector (ex.480 nm; em. 535 nm) which added 10 $\mu$M muscarine after 8 s. The data were acquired at 1 Hz and all data were normalized to the initial baseline fluorescence (2–5 s). The lines represent the average of 6 individual wells. (B)Identical to (A) except all wells were incubated with 3 $\mu$M BAPTA-AM and the indicated concentrations of atropine. Prior to addition of 10 $\mu$M muscarine, the VIPR read the fluorescence of each well for 5 s. To determine the stability of the fluorescence signal, there was a delay of 5 minutes after the addition of muscarine before the plate was read in the VIPR for another 5 s. The points represent the average and standard deviations of the change in fluorescence recorded in 8 individual wells.

Muscimol stimulated an endogenous muscarinic receptor (Moriya, H., Takagi, Y., Nakanishi, T., Hayashi, M., Tani, T., and Hirotsu, I. (1999) Affinity profiles of various muscarinic antagonists for cloned human muscarinic acetylcholine receptor (MACHR) subtypes and MACHRS in rat heart and submandibular gland. Life Sciences 25 2351–2358; Caulfield, M. P. (1993) Muscarinic receptors-characterization, coupling and function. Pharmac. Ther. 58, 319–379)in HEK-AEQ17 cells which gave a robust fluorescence signal when measured with fluo-4 using the VIPR. The kinetics of this calcium transient was different from that measured for either the VR1 or hGHSR1a calcium transient. Activation with muscimol (10 μM) caused a fast transient response, followed by a slower response (FIG. 9A). The fast transient response was very sensitive to BAPTA, and was eliminated by low levels of the chelator (3 μM BAPTA-AM), but a fluorescence signal could be detected under these conditions that was stable for at least 3 minutes. At a higher BAPTA concentration (10 μM BAPTA-AM), the increase in fluorescence was very slow and had not yet stabilized even after 3 minutes.

EXAMPLE 5

Measurement of Luminescence with Cells Expressing VR1

Cell Lines and Growth Conditions.

Parental HEK293 cell lines expressing apoaequorin (293AEQ17 cells) were used to develop stable clonal cell lines expressing the rat VR1 capsaicin receptor. The VR1 293AEQ17 were maintained on growth media containing DMEM (GIBCOBRL, high glucose, with L-glutamine, with 110 mg/L sodium pyruvate, with pyridoxine HCl), 25 mM HEPES (GIBCOBRL, 1M stock), 0.5 mg/mL geneticin (GIBCOBRL, 50 mg/mL stock), 1 μg/mL puromycin (CLONTECH), and 10% fetal bovine serum (GEMINI BIO-PRODUCTS, heat inactivated) at 37° C., 10% $CO^2$.

Preparation of Cells for Assay

Cells were grown to 80–95% confluence in tissue culture flasks (T-225, Corning) and harvested by trypsinization (Trypsin/EDTA, GIBCOBRL). Cells were dispensed (about $1 \times 10^5$ cells/0.2 ml/well) into 96-well white clear-bottom BIOCOAT poly-D-lysine plates (BECTON DICKENSON, Bedford, Mass.) in growth media and incubated overnight at 37° C. in a humidified incubator at 10% $CO^2$. Cells were charged with the aequorin substrate, coelenterazine h (MOLECULAR PROBES, #C-6780), by removing the growth media and incubating the cells with 75 μl of charge buffer (DMEM GIBCOBRL #12320-032; 0.1% FBS GEMINI BIO-PRODUCTS, Inc. #100–107;5 μM coelenterazine h; 30 μM reduced glutathione) for 2 hours at 37° C., 10% $CO^2$. The charge buffer was then removed and the cells were washed twice with 100 μl of enriched-PBS (pH 7.2) and then incubated with 100 μl of enriched-PBS supplemented with 0–30 μM BAPTA-AM for 30–120 min at 37° C., 10% $CO^2$. The cells were then washed and loaded with 100 μg of enriched-PBS with or without the indicated antagonist. The calcium response was initiated by addition of 100 μl of the indicated concentration of capsaicin (SIGMA #M2028) to the wells by a WALLAC MICROBETA JET. In order to obtain more consistent kinetics, the Jet was set to simultaneously read only six wells per determination.

Figure 7A:
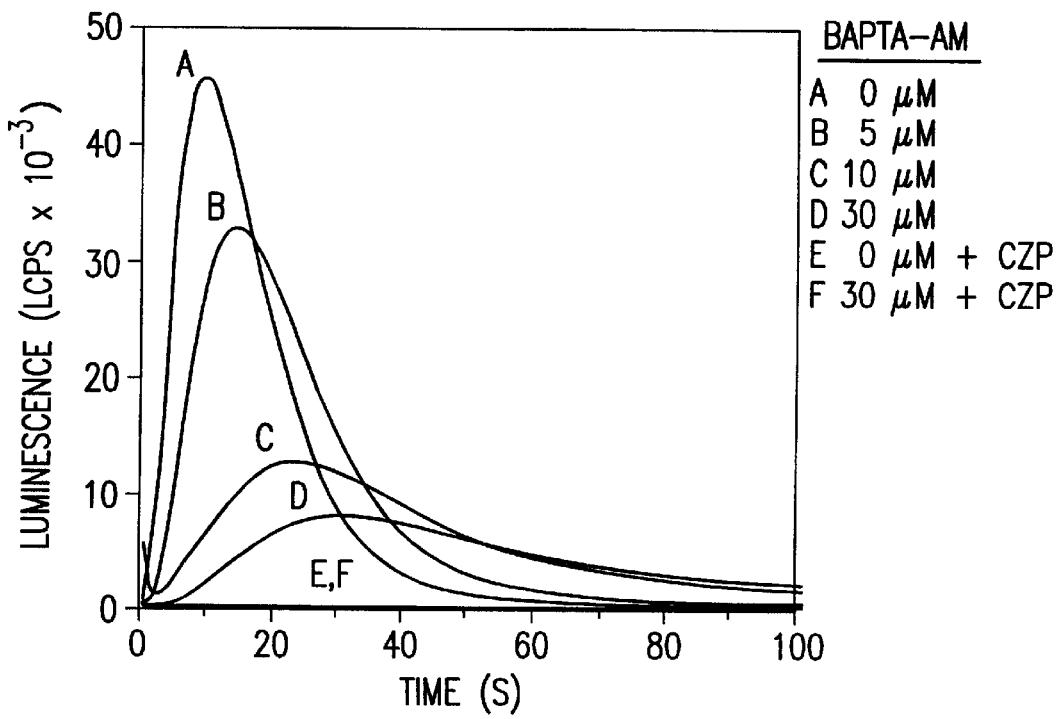
FIGS. 7(A and B) shows that BAPTA delays the calcium response in VR1 cells as measured by aequorin luminescence. VR1 was stably expressed in HEK-293 cells that also express apoaequorin. The cells were grown in 96-well assay plates overnight and then incubated for 2 hours with the substrate coelenterazine (5 $\mu$M) to convert apoaequorin to aequorin. The cells were washed with PBS and then incubated with the indicated concentration of BAPTA-AM for 30 minutes. After a PBS wash, the cells had either PBS or 50 $\mu$M capsazepine added for 30 minutes or more. The plates were then read on a WALLAC MICROBETA JET luminometer. (A) Data were acquired at 1 Hz after addition of 50 nM capsaicin. The data are the average of six individual wells. (B) In parallel experiments, the time at which peak luminescence occurred (average of six determinations) after incubation with the indicated BAPTA-AM concentrations was plotted versus the capsaicin concentration added by the WALLAC MICROBETA JET.
Figure 7B:
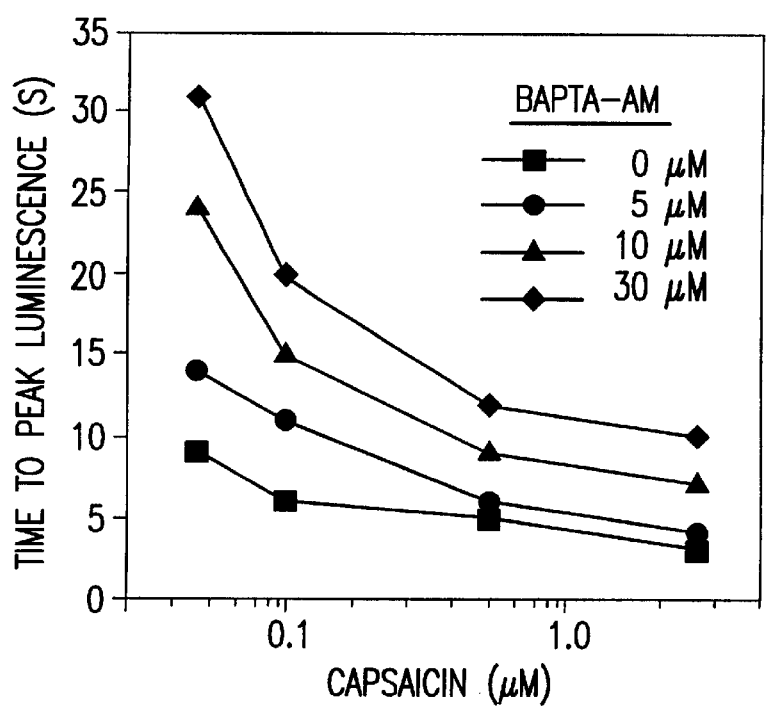

The aequorin flash luminescence response upon activation of VR1 was not as easily delayed by intracellular BAPTA, as was the fluo-3 fluorescence signal. For these experiments, the kinetics of the flash luminescence were followed using a WALLAC MICROBETA JET luminometer that injects reagent and records light emission from six wells of a 96-well plate simultaneously. Addition of capsaicin (50 nM) caused a rapid and transient luminescence signal that was largely complete within 30 seconds, with a peak level occurring in only about 10 sec (FIG. 7A). The addition of increasing levels of BAPTA (0–30 μM BAPTA-AM) caused a progressive delay in the onset of the aequorin luminescence signal, with a maximum response at 30 sec, delayed from 10 sec. This signal was extended for up to 3 minutes, the maximum time recorded. For these experiments, it was important to use a low concentration of agonist because at high agonist concentration (0.5 μM) even 30 μM BAPTA-AM only delayed the peak response from about 5 sec to 10 sec (FIG. 7B).

While the kinetics of the aequorin-response were altered by buffering with BAPTA, the overall signal was not significantly suppressed as the total signal at a given agonist concentration did not significantly vary using 0 μM to 30 μM BAPTA-AM.

EXAMPLE 6

Measurement of Luminescence with Cells Expressing Growth Hormone Secretagogue Receptor 1a Cell Lines and Growth Conditions.

Parental HEK293 cell lines expressing apoaequorin (293AEQ17 cells) were used to develop stable clonal cell lines expressing the human growth hormone secretagogue receptor type 1a (hGHSR1A). The hGHSR1A cells were maintained on growth media containing DMEM (GIBCOBRL, high glucose, with L-glutamine, with 110 mg/L sodium pyruvate, with pyridoxine HCl), 25 mM HEPES (GIBCOBRL, 1M stock), 0.5 mg/mL geneticin (GIBCOBRL, 50 mg/mL stock), 0.2 mg/mL hygromycin (BOEHRINGER MANNHEIM), and 10% fetal bovine serum (HYCLONE, defined) at 37° C., 10% $CO^2$.

Preparation of Cells for Assay

Cells were grown to 80–95% confluence in tissue culture flasks (T-225, Corning) and harvested by trypsinization (Trypsin/EDTA, GIBCOBRL). Cells were dispensed (about $1\times10^5$ cells/0.2 ml/well) into 96-well white clear-bottom BIOCOAT poly-D-lysine plates (BECTON DICKENSON, Bedford, Mass.) in growth media and incubated overnight at 37° C. in a humidified incubator at 10% $CO^2$. Cells were charged with the aequorin substrate, coelenterazine h (MOLECULAR PROBES, #C-6780), by removing the growth media and incubating the cells with 75 μl of charge buffer (DMEM GIBCOBRL#12320-032; 0.1% FBS GEMINI BIO-PRODUCTS, Inc. #100-107; 5 μM coelenterazine h; 30 μM reduced glutathione) for 2 hours at 37° C., 10% $CO^2$. The charge buffer was then removed and the cells were washed twice with 100 μl of enriched-PBS (pH 7.2) and then incubated with 100 μl of enriched-PBS supplemented with 0–30 μM BAPTA-AM for 30–120 min at 37° C., 10% $CO^2$. The cells were then washed and loaded with 100 μl of enriched-PBS with or without the indicated antagonist. The calcium response was initiated by addition of 100 μl of the indicated concentration of ghrelin (PHOENIX PHARMACEUTICALS #031031) by a WALLAC MICROBETA JET. In order to obtain more consistent kinetics, the Jet was set to simultaneously read only six wells per determination.

Figure 8B:
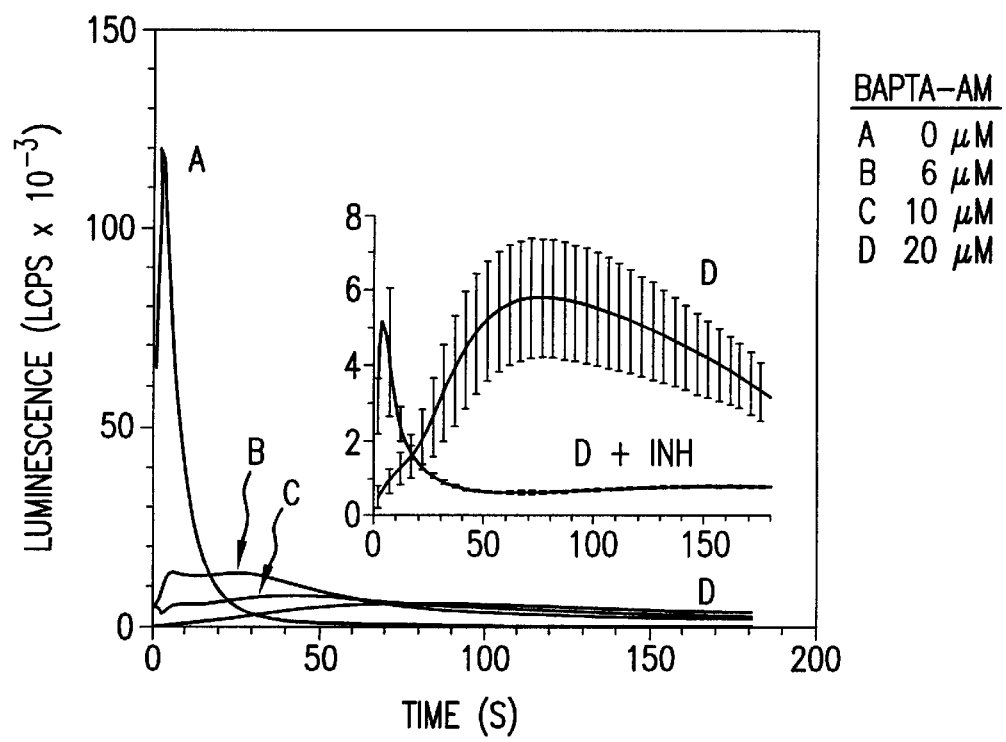

Upon addition of the hGSHR1a agonist (100 nM ghrelin), there was a rapid increase in light emission that peaked in only 3 sec and was essentially gone after 30 sec, as measured on the Jet luminometer (FIG. 8B). In contrast, the addition of BAPTA (30 μM BAPTA-AM) decreased the luminescence signal to only about 5% of the response in the absence of BAPTA, but time to reach the maximum light emission was delayed to 75 sec (FIG. 8B insert). In addition, while the amplitude of the signal was reduced, there was a significant window between the signal in the absence and presence of antagonist that can be used in a screening assay.

EXAMPLE 7

Manual Measurements of Fluorescence with Muscarinic Acetylcholine Receptors

Cell Lines and Growth Conditions.

Parental HEK293 cell lines expressing apoaequorin (293AEQ17 cells) were maintained on growth media containing DMEM (GIBCOBRL, high glucose, with L-glutamine, with 110 mg/L sodium pyruvate, with pyridoxine HCl), 25 mM HEPES (GIBCOBRL, 1M stock), 0.5 mg/mL geneticin (GIBCOBRL, 50 mg/mL stock), and 10% fetal bovine serum (GEMINI BIO-PRODUCTS, heat inactivated) at 37° C., 10% $CO^2$.

Preparation of Cells for Assay

Cells were grown to 80–95% confluence in tissue culture flasks (T-225, Corning) and harvested by trypsinization (Trypsin/EDTA, GIBCOBRL). Cells were dispensed (about $1\times10^5$ cells/0.2 ml/well) into 96-well black clear-bottom BIOCOAT poly-D-lysine plates (BECTON DICKENSON, Bedford, Mass.) in growth media and incubated overnight at 37° C. in a humidified incubator at 10% $CO^2$. Cells were washed once with 200 μs of enriched PBS (Dulbecco's PBS (GIBCOBRL #14040-117), 10 mM HEPES, 2 g/L glucose; pH 7.2) and then incubated with 100 μl of 5 μM fluo-4-AM (MOLECULAR PROBES #F14202) with or without of 1,2-bis(o-aminophenoxy)ethane-N,N,N',N'-tetraacetic acid tetra(acetoxymethyl) ester (BAPTA-AM, MOLECULAR PROBES #B1205) in enriched PBS containing 0.02% pluronic F-127 (MOLECULAR PROBES #P-3000) for 30–70 minutes. Wells were washed two times with 100 μl of enriched-PBS, and then 100 μl enriched-PBS with or without antagonist was added for 30 minutes prior to assay on the AURORA fluorescence plate reader VIPR (ex. 480 nm, em. 535 nm). The calcium response was initiated by addition of 100 μl of the indicated concentration of (+/−)-muscarine (SIGMA #M0405) using a handheld device. The VIPR instrument was used to measure a 5 sec initial fluorescence, and then to record another 5 sec fluorescence response after a delay of 5 minutes.

Kinetic experiments using the VIPR and Jet instruments demonstrate that low levels of intracellular BAPTA can delay and extend calcium responses in a variety of functional assays for ion channels and GPCR's. An empirical approach is required initially to balance the concentration of the chelator and agonist used, but in each case a useful fluorescence-based or aequorin-based assay was developed with an extended calcium response.

A useful application of this invention is to develop assay conditions which would extend the transient calcium signal sufficiently to allow measurement of the fluorescence or luminescence by standard laboratory plate readers. To replace instruments used above, having simultaneous liquid addition and recording, an observable signal must be maintained following addition of agonist on the order of several minutes. Based on the results from these kinetic experiments, it was tested whether one could add agonist to a 96-well plate with a hand-held pipetting device and then transfer the plate to an appropriate reader and still maintain a stable signal over background suitable for developing HTS assays.

Figure 9B:
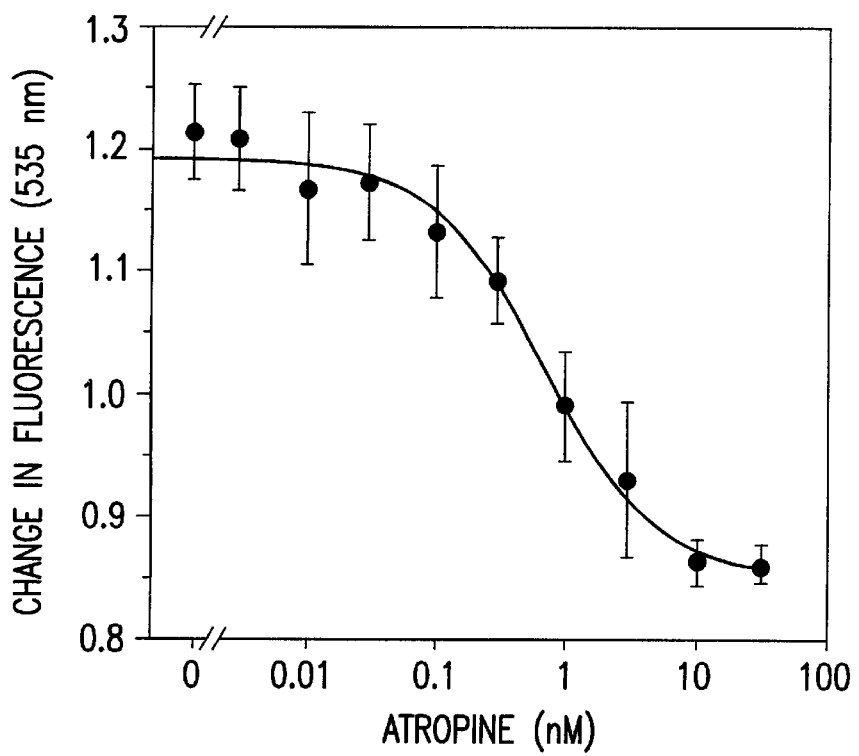

A plate of HEK-AEQ17 cells was loaded with 5 μM Fluo-4 and 3 μM BAPTA-AM. An initial fluorescence measurement was taken using the VIPR (5 sec) and then muscimol (10 μM) was added to the plate by hand using a multichannel pipet to activate the endogenous muscarinic AChR. The plate was incubated for 5 minutes before taking a second fluorescence reading using the VIPR (5 sec). Even 5 minutes after stimulation with muscimol, a clear increase in the fluorescence signal was detected. Under these conditions a dose dependent decrease in the fluorescence signal was observed with atropine, giving a $K_I$=0.7 nM, which was close to the expected potency for atropine (FIG. 9B).

EXAMPLE 8

Manual Measurement of Luminescence with Cells Expressing VR1

Cell Lines and Growth Conditions.

Parental HEK293 cell lines expressing apoaequorin (293AEQ17 cells) were used to develop stable clonal cell lines expressing the rat VR1 capsaicin receptor. The VR1 293AEQ17 and parental 293AEQ17 cells were maintained on growth media containing DMEM (GIBCOBRL, high glucose, with L-glutamine, with 110 mg/L sodium pyruvate, with pyridoxine HCl), 25 mM HEPES (GIBCOBRL, 1M stock), 0.5 mg/mL geneticin (GIBCOBRL, 50 mg/mL stock), 1 μg/mL puromycin (CLONTECH), and 10% fetal bovine serum (GEMINI BIO-PRODUCTS, heat inactivated) at 37° C., 10% $CO^2$.

Preparation of Cells for Assay

Cells were grown to 80–95% confluence in tissue culture flasks (T-225, Corning) and harvested by trypsinization (Trypsin/EDTA, GIBCOBRL). Cells were dispensed (about $1\times10^5$ cells/0.2 ml/well) into 96-well white clear-bottom BIOCOAT poly-D-lysine plates (BECTON DICKENSON, Bedford, Mass.) in growth media and incubated overnight at 37° C. in a humidified incubator at 10% $CO^2$. Cells were charged with the aequorin substrate, coelenterazine h (MOLECULAR PROBES, #C-6780), by removing the growth media and incubating the cells with 75 µl of charge buffer (DMEM GIBCOBRL#12320-032; 0.1% PBS GEMINI BIO-PRODUCTS, Inc. #100-107; 5 µM coelenterazine h; 30 µM reduced glutathione) for 2 hours at 37° C., 10% $CO^2$. The charge buffer was then removed and the cells were washed twice with 100 µl of enriched-PBS (pH 7.2) and then incubated with 100 µl of enriched-PBS supplemented with 0 or 10 µM BAPTA-AM for 30 min at 37° C., 10% $CO^2$. The cells were then washed and loaded with 100 µl of enriched-PBS with or without the indicated antagonist. The calcium response was initiated by addition of 100 µl of the indicated concentration of capsaicin (SIGMA #M2028) to the appropriate set of six wells using a handheld device. The WALLAC MICROBETA JET was used to measure 10 sec of luminescence after a delay of 2 minutes.

Figure 10A:
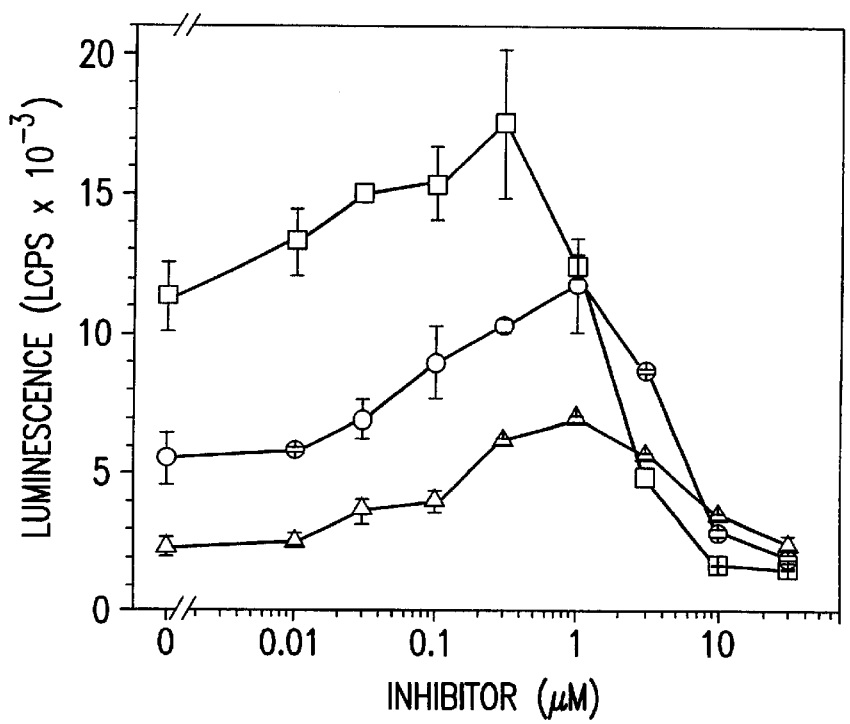
FIGS. 10(A and B) shows the inhibition of luminescence responses measured 2 minutes after adding ghrelin or capsaicin. Cells were prepared for luminescence reading on the WALLAC MICROBETA JET as described in FIG. 3 with either no BAPTA-AM (Δ), 3 $\mu$M BAPTA-AM (○), or 10 $\mu$M BAPTA-AM (□). (A) hGHSR1A cells incubated with the indicated concentrations of L-756,867. (B) VR1 cells incubated with the indicated concentration of capsazepine. (A) Ghrelin (100 nM) or 0.5 $\mu$M capsaicin (B) was added manually to six wells and after 2 minutes the luminescence was read for 10 s. Each point is the average and standard deviation of 1–10 determinations.
Figure 10B:
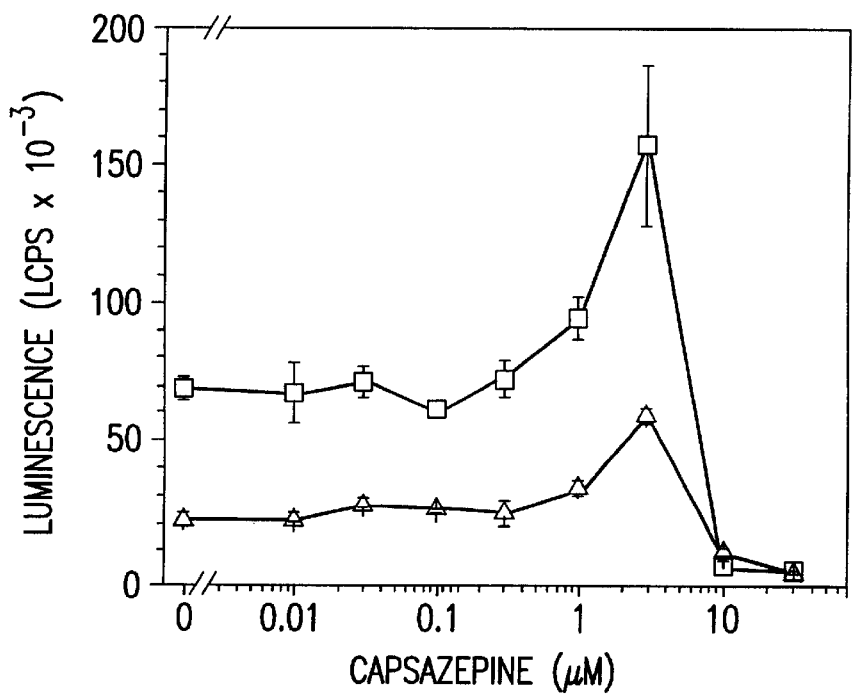

VR1 cells were charged with coelenterazine, treated with or without BAPTA-AM, and then incubated with increasing concentrations of the antagonist capsazepine. Using a handheld multichannel pipet, capsaicin (0.5 uM) was added to the 96-well plates containing the VR1 expressing cells (FIG. 10B). After a lapse of two minutes, the plates were read using the WALLAC MICROBETA JET luminometer. Complex dose-response curves were observed for the antagonist capsazepine. The luminescence signal actually increased with antagonist concentration up to a point, but at higher concentrations was completely blocked. This complex dose-response curve was observed both in the presence and absence of BAPTA. Yet overall, the addition of BAPTA increased the luminescence such that a 4-fold signal over background could be measured 2 minutes after stimulation with agonist. Moreover, the receptor antagonists displayed the expected potency in the presence of BAPTA.

In order to better understand the complexity of the dose-response curves, the kinetics of the aequorin luminescence in the VR1 HEK293-AEQ cells were examined in the presence of increasing concentrations of antagonist. It was found that the antagonist itself at sub-saturating concentrations caused a delay in the calcium signal in the absence of chelator. Presumably, the delayed kinetics are attributable to the competition between the agonist and antagonist for the receptor. This is distinctly different from the mechanism by which BAPTA delays the luminescence which is due to chelation of calcium. While the mechanism is different, the results indicate that a known antagonist might also be used to delay the calcium transient. However, the use of an intracellular chelator should be more universally applicable to any calcium-based functional assay.

EXAMPLE 9

Manual Measurement of Luminescence with Cells Expressing Growth Hormone Secretagogue Receptor 1a Cell Lines and Growth Conditions.

Parental HEK293 cell lines expressing apoaequorin (293AEQ17 cells) were used to develop stable clonal cell lines expressing the human growth hormone secretagogue receptor type 1a (hGHSR1A). The hGHSR1A cells were maintained on growth media containing DMEM (GIBCOBRL, high glucose, with L-glutamine, with 110 mg/L sodium pyruvate, with pyridoxine HCl), 25 mM HEPES (GIBCOBRL, 1M stock), 0.5 mg/mL geneticin (GIBCOBRL, 50 mg/mL stock), 0.2 mg/mL hygromycin (BOEHRINGER MANNHEIM), and 10% fetal bovine serum (HYCLONE, defined) at 37° C., 10% $CO^2$.

Preparation of Cells for Assay

Cells were grown to 80–95% confluence in tissue culture flasks (T-225, Corning) and harvested by trypsinization (Trypsin/EDTA, GIBCOBRL). Cells were dispensed (about $1\times10^5$ cells/0.2 ml/well) into 96-well white clear-bottom BIOCOAT poly-D-lysine plates (BECTON DICKENSON, Bedford, Mass.) in growth media and incubated overnight at 37° C. in a humidified incubator at 10% $CO^2$. Cells were charged with the aequorin substrate, coelenterazine h (MOLECULAR PROBES, #C-6780), by removing the growth media and incubating the cells with 75 µl of charge buffer (DMEM GIBCOBRL #12320-032; 0.1% FBS GEMINI BIO-PRODUCTS, Inc. #100-107;5 µM coelenterazine h; 30 µM reduced glutathione) for 2 hours at 37° C., 10% $CO^2$. The charge buffer was then removed and the cells were washed twice with 100 µl of enriched-PBS (pH 7.2) and then incubated with 100 µl of enriched-PBS supplemented with 0–10 µM BAPTA-AM for 30 min at 37° C., 10% $CO^2$. The cells were then washed and loaded with 100 µl of enriched-PBS with or without the indicated antagonist. The calcium response was initiated by addition of 100 µl of the indicated concentration of ghrelin (Phoenix pharmaceuticals #031031) to the appropriate set of six wells using a handheld device. The WALLAC MICROBETA JET was used to measure 10 sec of luminescence after a delay of 2 minutes.

hGHSR1a cells were charged with coelenterazine, treated with or without BAPTA-AM, and then incubated with increasing concentrations of the antagonist L-756,867 (Smith, R. G., Griffin, P. R., Xu, Y., Smith, A. G. A., Liu, K., Calacay, J., Feighner, S. D., Pong., C.-S., Leong, D., Pomes, A., Cheng, K., Van der Ploeg, L. H. T., Howard, A. D., Schaeffer, J., & Leonard, R. J. (2000) Adenosine: A partial agonist of the growth hormone secretagogue receptor. *Biochem. Biophys. Res. Commun.* 276, 1306–1313; Bednarek, M. A., Feighner, S. C., Pong, S.-S., McKee, K. K., Hreniuk, D. L., Silva, M. V., Warren, V. A., Howard, A. D., Van der Ploeg, L. H. Y., and Heck J. V. (2000) Structure-function studies on the new growth hormone-releasing peptide, ghrelin: Minimal sequence of ghrelin necessary for activation of growth hormone secretagogue receptor 1a. *J. Med Chem.* 43 4370–4376). Using a handheld multichannel pipet, ghrelin (100 nM) was added to the 96-well plates containing the hGHSR1a cells (FIG. 10A). After a lapse of two minutes, the plates were read using the WALLAC MICROBETA JET luminometer. The luminescence signal actually increased with antagonist concentration up to a point, but at higher concentrations was completely blocked. These complex dose-response curves were observed both in the presence and absence of BAPTA. Yet overall, the addition of BAPTA increased the luminescence such that a 6-fold signal over background could be measured 2 minutes after stimulation with agonist. Moreover, the receptor antagonists displayed the expected potency in the presence of BAPTA.

Discussion

Low levels of an intracellular chelator, BAPTA, can slow the kinetics of calcium transients generated from influx through a plasma membrane ion channel (VR1) or release from intracellular stores ($InsP_3$-gated channels). In the preferred embodiments described herein, the cell permeable acetoxy methyl ester of the calcium chelator, BAPTA, was used because it is available commercially and can be easily loaded into cells cultured in 96-well plates. The calcium binding kinetics and potency of many calcium chelators have been measured and shown to bind rapidly ($2-8\times10^8$ $M^{-1}s^{-1}$), but with widely variable off-rates ($100-10,000$ $s^{-1}$) and affinities. These include fluorescent calcium probes such as fura-2, and the nonfluorescent chelator BAPTA, employed here. The most commonly used calcium chelators, EDTA and EGTA, bind and release calcium much more slowly (100-fold) compared to BAPTA and may not be as effective as BAPTA in delaying the very rapid changes in calcium generated by the VR-1 channel.

The calcium responses could be completely blocked at sufficiently high concentrations of BAPTA-AM as expected. The data demonstrate that it is important to balance the receptor stimulation and intracellular BAPTA concentration. Since the intracellular BAPTA concentration is determined by several factors including, among others, incubation time, temperature, and cell type , the BAPTA-AM concentration used should be titrated carefully.

There are many other calcium chelators described in the literature as well as calcium binding proteins which may be employed in delaying the response measured by calcium sensitive reporters. For example, one may generate stable cell lines expressing calcium-binding proteins, eliminating the need for loading cells with BAPTA-AM.

Following the teaching of this description of the invention, one need only test any particular chelator or binding protein to determine the appropriate concentration that effectively provides a window that can be employed in the design of a high throughput assay. Any particular chelator or binding protein can be chosen based on it's properties including, for example, availability within a cell, calcium affinity and rate of release of calcium, and overall performance in delaying a fluorescent or luminescent signal.

What is claimed is:

1. A method for determining whether a candidate compound is an agonist or an inhibitor of a protein using cells that contain a calcium sensitive reporter comprising the steps of:

(a) providing cells that express the protein and contain a calcium sensitive reporter;

(b) exposing the cells to an intracellular chelator of calcium;

(c) exposing a first portion of the cells to a compound;

(d) measuring the signal generated in the first portion;

(e) measuring the signal generated in a second portion of the cells that was not exposed to the compound, and (f) comparing the amount of signal in the first and second portions of the cells where an increase in the amount of signal in the presence of the compound indicates that the compound is an agonist of the protein and a decrease in the amount of signal in the presence of the compound indicates that the compounds is a inhibitor of the protein, wherein the signal generated by the calcium sensitive reporter is delayed by the presence of the intracellular chelator of calcium.

2. The method of claim 1 wherein step (a) comprises providing cells that are transiently transfected with an expression vector that directs the expression of the protein.

3. The method of claim 1 wherein the reporter is a protein.

4. The method of claim 3 wherein the cells are transiently transfected with an expression vector that directs the expression of the reporter.

5. The method of claim 3 wherein a polynucleotide that directs the expression of the reporter is stably integrated into the genome of the cells.

6. The method of claim 3 wherein the reporter is aequorin.

7. The method of claim 1 wherein the calcium sensitive reporter is an organic compound.

8. The method of claim 1 wherein the intracellular chelator of calcium is 1,2 bis(o-aminophenoxy)ethane-N,N,N', N',-tetraacetic acid tetra(acetoxymethyl)ester.

9. The method of claim 1 wherein the protein is a G-Protein Coupled Receptor or an ion channel.

10. The method of claim 1 wherein the protein is a receptor that is coupled to a calcium channel.

* * * * *